United States Patent
Bobo et al.

(10) Patent No.: US 6,673,022 B1
(45) Date of Patent: Jan. 6, 2004

(54) GAS COLUMN PRESSURE MONITORING CATHETERS

(75) Inventors: Donald Bobo, Fountain Valley, CA (US); James Gerg, Lake Forest, CA (US)

(73) Assignee: InnerSpace Medical, Inc., Santa Ana, CA (US)

( * ) Notice: Subject to any disclaimer, the term of this patent is extended or adjusted under 35 U.S.C. 154(b) by 0 days.

(21) Appl. No.: 09/618,495

(22) Filed: Jul. 18, 2000

Related U.S. Application Data

(63) Continuation-in-part of application No. 09/379,282, filed on Aug. 20, 1999, now abandoned.

(51) Int. Cl.[7] .................................................. A61B 5/00
(52) U.S. Cl. ...................................... 600/561; 600/587
(58) Field of Search ................................ 600/485, 486, 600/487, 488, 561, 587; 73/700, 706, 748, 756; 604/96.01, 264

(56) References Cited

U.S. PATENT DOCUMENTS

| | | | |
|---|---|---|---|
| 4,227,420 A | | 10/1980 | Lamadrid ..................... 73/756 |
| 4,300,571 A | | 11/1981 | Waldbillig .................. 600/486 |
| 4,314,480 A | | 2/1982 | Becker ......................... 73/706 |
| 4,648,406 A | | 3/1987 | Miller ......................... 600/487 |
| 4,705,499 A | * | 11/1987 | Hooven ....................... 600/561 |
| 4,841,984 A | | 6/1989 | Armeinades et al. ........ 600/561 |
| 4,944,307 A | * | 7/1990 | Hon et al. ................... 600/561 |
| 5,105,820 A | | 4/1992 | Moriuchi et al. ............ 600/488 |
| 5,573,007 A | | 11/1996 | Bobo, Sr. |
| 5,947,991 A | * | 9/1999 | Cowan ........................ 606/191 |
| 5,951,497 A | * | 9/1999 | Wallace et al. ............. 600/587 |
| 5,984,879 A | * | 11/1999 | Wallace et al. ............. 600/587 |
| 6,018,094 A | * | 1/2000 | Fox .............................. 623/11 |
| 6,080,134 A | * | 6/2000 | Lotti et al. .................. 604/175 |
| 6,083,179 A | * | 7/2000 | Oredsson .................... 600/587 |

FOREIGN PATENT DOCUMENTS

| | | |
|---|---|---|
| DE | 195 01 682 C1 | 2/1996 |
| WO | WO 82/02657 A1 | 8/1982 |
| WO | WO 86/03957 A1 | 7/1986 |
| WO | WO 90/11717 A1 | 10/1990 |
| WO | WO 96/04846 A1 | 2/1996 |

* cited by examiner

*Primary Examiner*—Charles A. Marmor, II
(74) *Attorney, Agent, or Firm*—Inskeep IP Group, Inc.

(57) ABSTRACT

A catheter has a pressure sensitive bladder at a distal end and a pressure transducer at a proximal end with the proximal end attached to a mammalian body and the bladder inserted within the mammalian body. The bladder partially filled with a gas responds to pressure changes within the body and the pressure transducer senses the changes via gaseous communication with the bladder. In one embodiment, the bladder is inserted in a human brain with the transducer mounted on a bolt affixed to the skull. Initial dissection of the brain tissue is effected by over-inflation of the bladder by a manual piston pump or a blunt ended slender rod. The transducer may be mounted on a bolt inserted within a hole drilled in the skull. An antimicrobial agent may be dispersed from openings in a seal between the bolt and the skull, from a porous seal, or from a ribbed or threaded outer surface of the bolt. In one embodiment, the catheter is inserted through an inner opening in the bolt and a drain may also be inserted through the bolt. In another embodiment, the pressure transducer is attached to the neck or shoulder area of a patient and a flexible catheter connects the transducer to a bladder inserted in the brain of a patient. The flexible catheter runs under a patch of skin on the skull and into a hole drilled through the skull to prevent bacteria entering the brain. The transducer may be attached anywhere on the body adjacent to an opening into the body wherein the bladder is inserted in the opening and communicates with the transducer through a short flexible catheter.

46 Claims, 8 Drawing Sheets

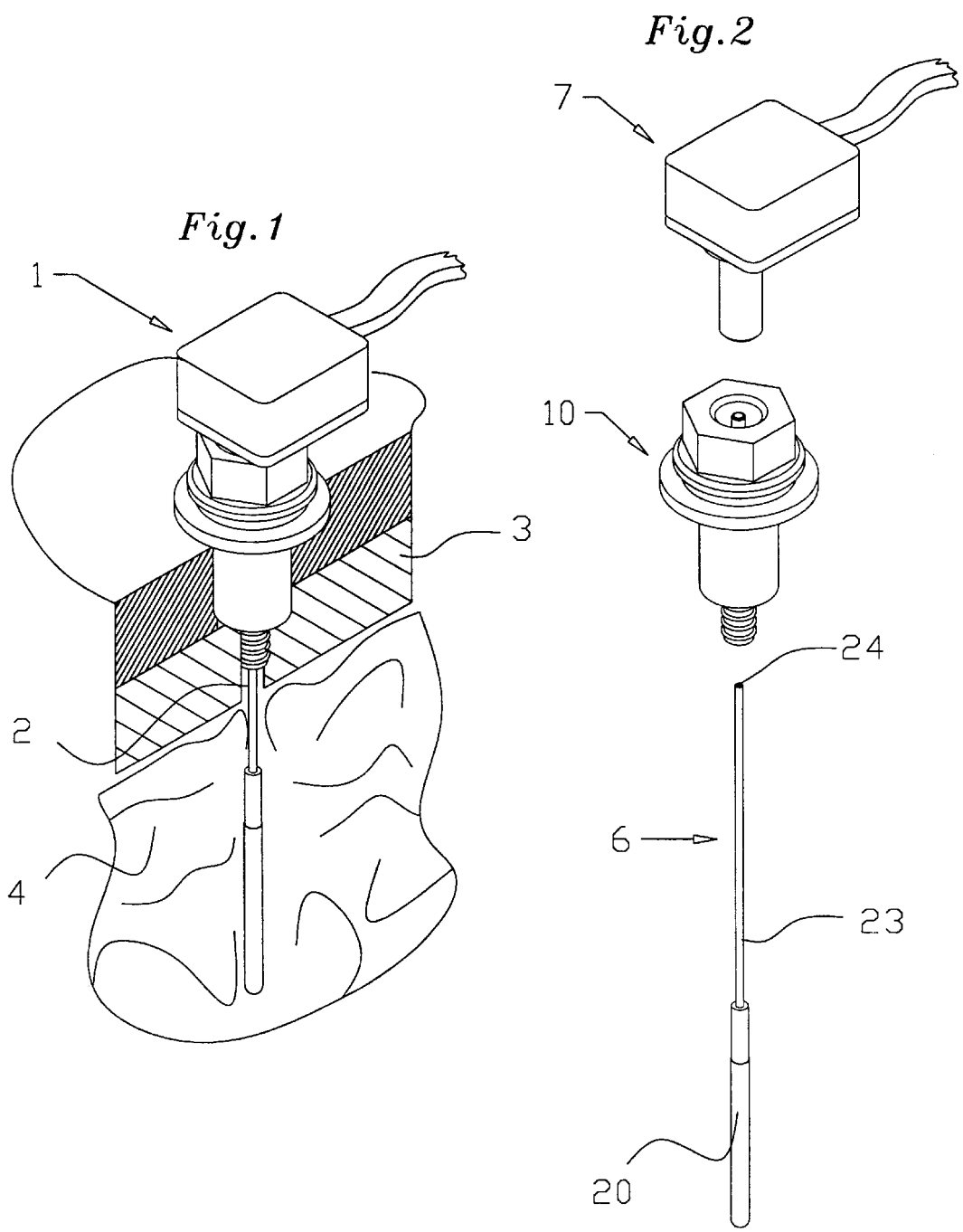

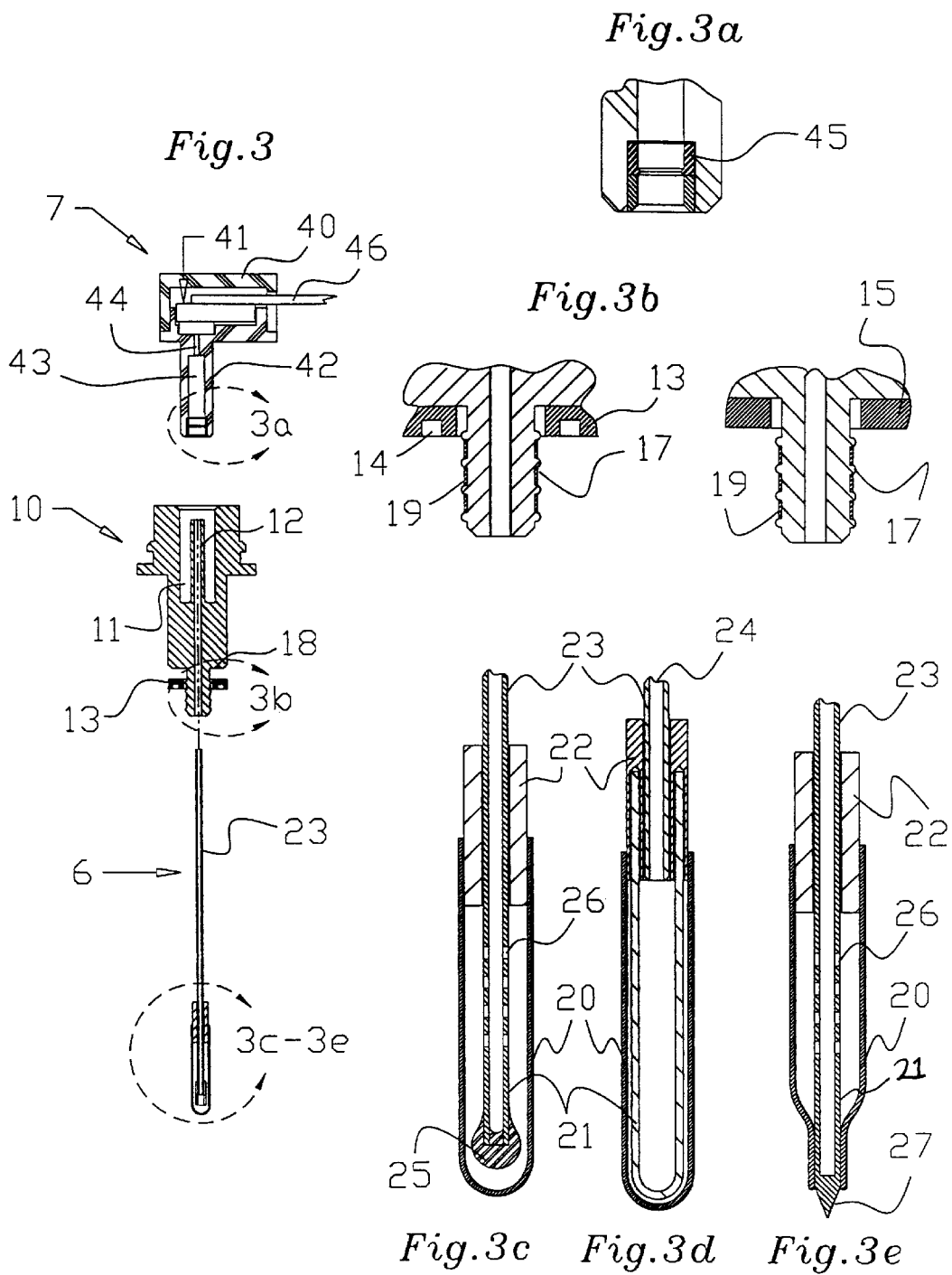

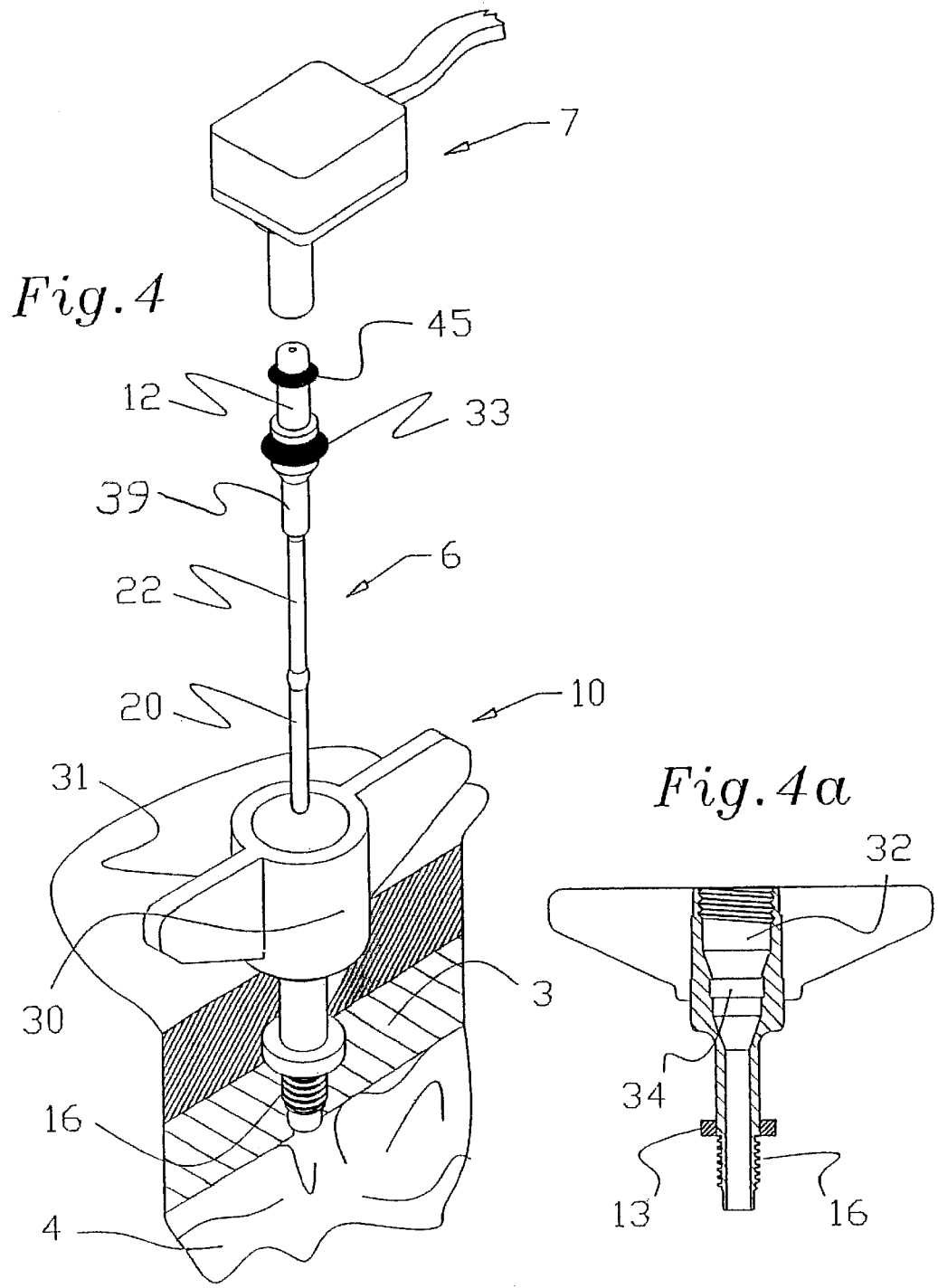

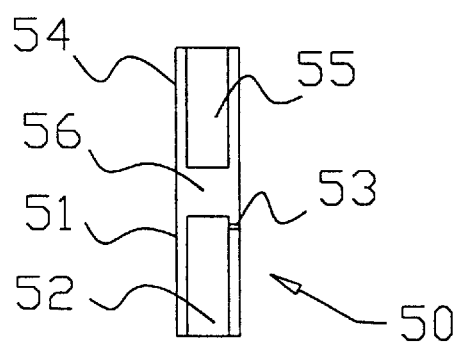
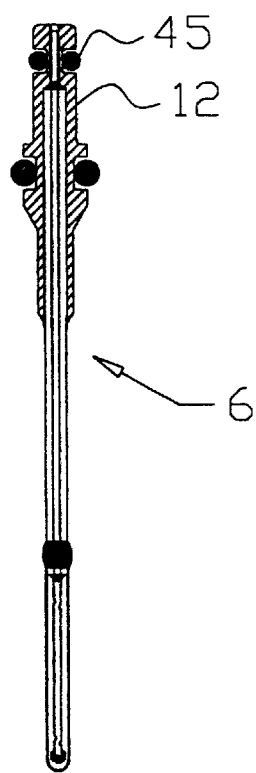
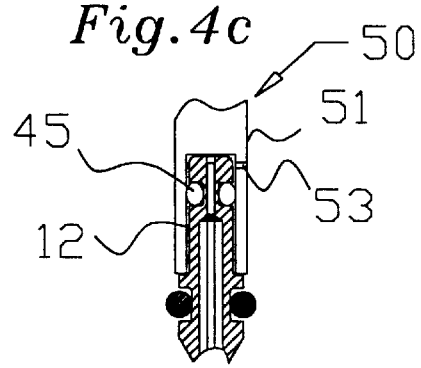
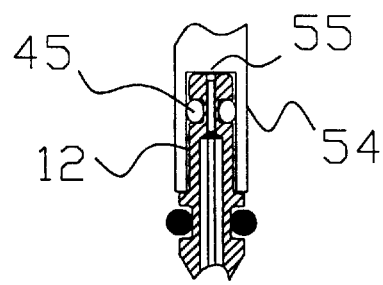
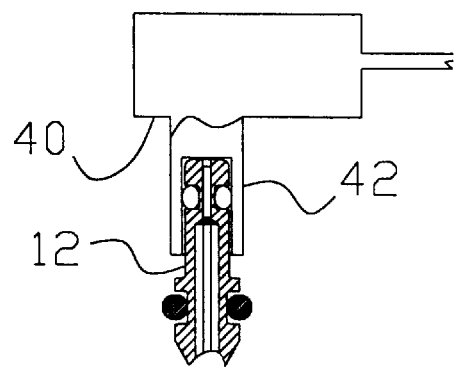

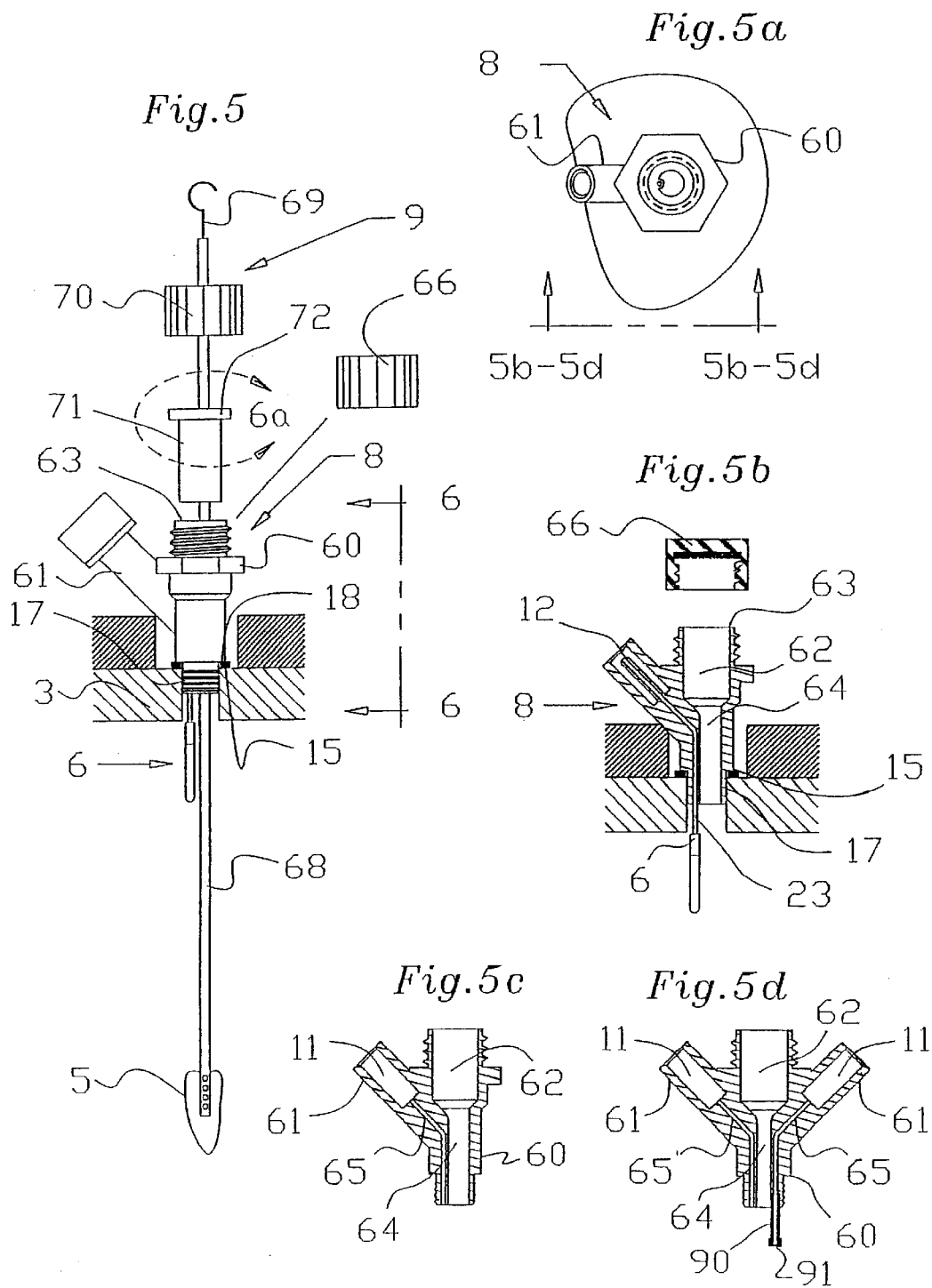

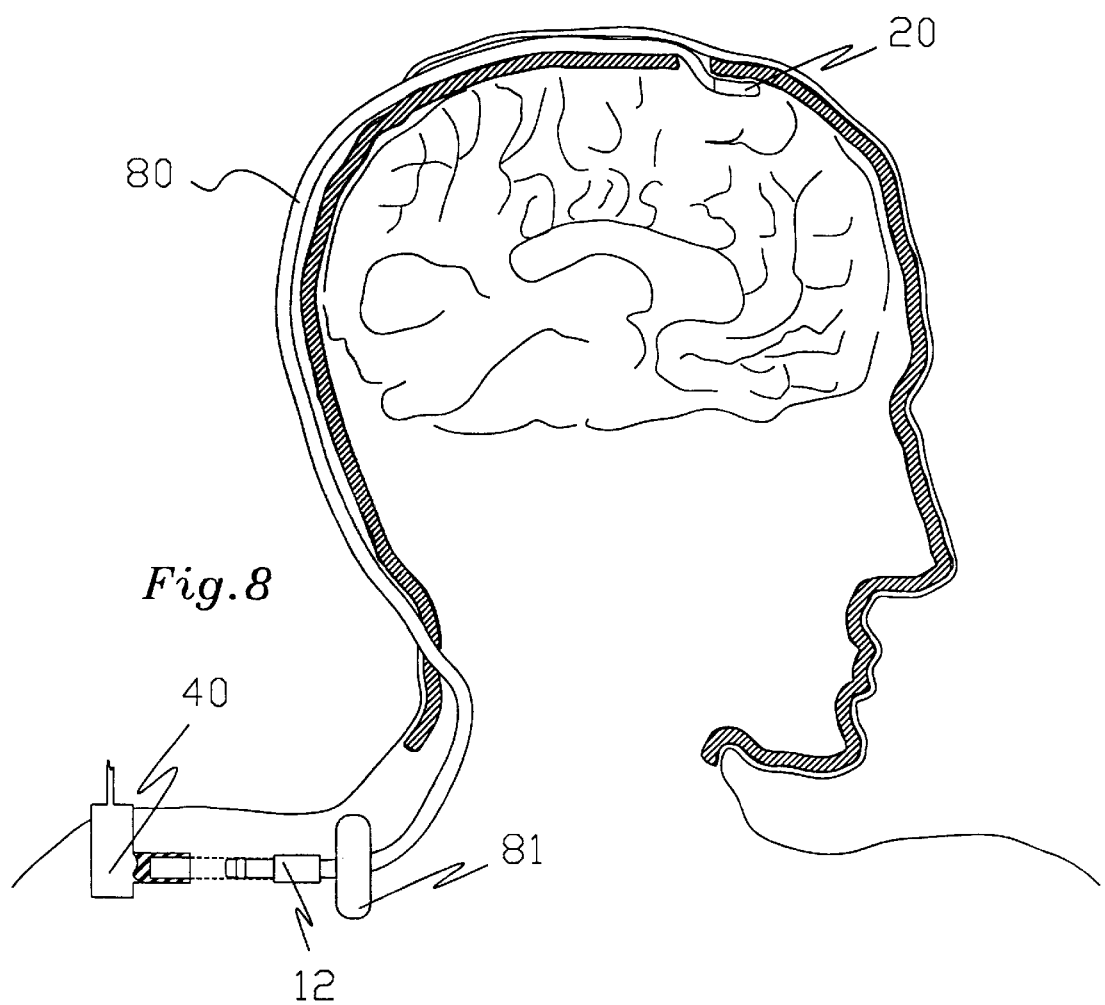
*Fig.8*
*Fig.8a*  *Fig.8b*

GAS COLUMN PRESSURE MONITORING CATHETERS

REFERENCES APPLICATIONS

This application is a continuation-in-part of copending application Ser. No. 09/379,282 filed Aug. 20, 1999 now abandoned.

BACKGROUND OF THE INVENTION

1. Field of the Invention

This invention relates to air-based catheter systems for monitoring pressure in a mammalian body especially as applied to measuring intracranial pressure (ICP) in the brain.

2. Description of the Prior Art

An air-based catheter consists of a catheter with an air lumen that communicates with a bladder at or near its distal end and with a connector at or near its proximal end. The bladder volume of the catheter changes as pressure changes in accordance with $P_1V_1=P_2V_2$ and thereby causes the pressure of the gas within the catheter to equal that of the external environment surrounding the bladder. The media in which the bladder senses pressure must be able to move toward or away from the bladder to cause the requisite change in bladder volume. Movement of the media is not a problem when the bladder is immersed in a flowable liquid such as blood. There is a problem when brain tissue is the media in that brain tissue has a limited ability to move. An air-based catheter designed to measure ICP must limit the movement required of the bladder so that the distance the bladder wall moves as it portrays the wave form of a heart beat does not exceed the intrinsic ability of brain tissue to move.

The prior art system, one made by Spiegelberg Gmbh, has a long air line that connects the catheter bladder to a bedside instrument. The air line significantly increases total system volume and thereby increases the volume change required of the bladder to reflect a given pressure change. Spiegelberg addresses the limited ability of brain tissue to move by purposefully underfilling the bladder. The underfilled bladder approximates a flat profile when placed in the brain. The (x)(y) planar area created by the flattened profile of the bladder reduces the movement required of brain tissue in the z dimension and does so in direct proportion to the x and y dimensions. The planar area chosen is one that limits the wall movement required of the bladder to a value compatible with the ability of brain tissue to move. The planar area is defined by the potential volume of the bladder and the degree to which it is underfilled. Spiegelberg uses a 425-ul bladder filled about 25% full. The underfilled bladder makes it possible for the Spiegelberg air-based catheter to measure pressure in the brain. An electromechanical pump is used to address the limited operating life of a bladder with a large surface area and small contained volume.

The volume of air in the bladder displaces brain tissue. It is therefore desirable that the air volume be as small as possible to limit tissue displacement. In the Spiegelberg system, most of the system volume that must be acted upon by the bladder is contained in the long air line that connects the intracranial catheter to a bedside instrument housing a pressure transducer. The connecting line represents about 80% of the total system volume. It is therefore responsible for 80% of the air volume required by the bladder to accomplish the required volume change. Bladder volume and therefore brain trauma in prior art are therefore largely defined by the volume of air in the air line that connects the catheter to a bedside instrument. Furthermore, the volume of air in the connecting air line largely defines the potential volume of the oversized bladder required to achieve the underfilled state necessary to limit bladder wall movement in the Z direction. The surface area of the oversized bladder increases air lost by diffusion and decreases the operating life of the catheter, i.e., the period of time after which air lost by diffusion must be replaced.

Brain trauma caused by the air volume within the bladder can be minimized if the air in the system outside the bladder is held to a minimum. If Vnb=volume of non-bladder air and Vb=volume of bladder air, then system volume=(Vnb+Vb). As system volume changes from $V_1$ to $V_2$, $V_1-V_2$=(Vnb+$Vb_1$)−(Vnb+$Vb_2$). Vb is the only variable volume; therefore the change required of the bladder is least when the non-bladder air volume (Vnb) is zero. Accordingly, a design least demanding in terms of both bladder wall movement and volume of brain tissue displaced is one wherein the ratio of (system volume)÷(bladder volume) approaches 1:1. The ratio in the Spiegelberg device is 5:1, a ratio far from ideal. The 5:1 ratio calculation includes 550 ul of gas contained in the 154 cm long air line and approximately 125 ul of gas in the bladder for a total system volume of about 675 ul.

The patents and literature covering gas column pressure monitoring catheters describe systems designed for various pressure measurement applications. Catheters constructed according to these teachings, however, are not optimal for use in measuring intracranial pressure (ICP) in that they do not minimize brain trauma nor do away with the need for an electromechanical pump. The deficiencies, if addressed, would greatly improve the usefulness and safety of the catheter.

A number of prior art devices transmit physiological pressure through a gaseous medium. The following United Sates and foreign patents/patent publications have described pressure measuring catheters and other pressure transmitting systems wherein a gas is utilized as a pressure-transmitting medium in at least a portion of the system: U.S. Pat. No. 5,573,007 (Bobo), U.S. Pat. No. 2,840,069 (Squire et al), U.S. Pat. No. 4,227,420 (Lamadrid), U.S. Pat. No. 4,300,571 (Waldbilling), U.S. Pat. No. 4,314,480 (Becker), U.S. Pat. No. 4,648,406 (Miller), U.S. Pat. No. 4,841,984 (Armeniades et al.), U.S. Pat. No. 5,105,820 (Moriuchi, et al.), Patent publications: WO82/02657 (Ebert), WO86/03957 (Spiegelberg), WO90/11717 (Utah Medical Products, Inc.) Prior art pertaining specifically to a gas-column pressure-monitoring catheter that employs a flaccid bladder is explicitly covered in WO86/03957 (Spiegelberg) and U.S. Pat. No. 5,573,007 (Bobo).

The only prior art air-based catheter capable of measuring ICP in brain tissue is a device produced by Spiegelberg Gmbh in Germany. The Spiegelberg device addresses the matter of controlling bladder wall movement by using a partially filled bladder. The bladder has a potential volume of 425 ul net of the volume occupied by the catheter within. Once the bladder is inserted into the brain, an electromechanical pump defines ICP level. The pump then injects an amount of air into the bladder that ranges from 50 to 100 ul. The electromechanical pump deflates and refills the bladder on an hourly basis. The terms injected or filled as used hereinafter means the volume of gas inserted into the bladder where the pressure of the injected gas is equal to atmospheric pressure. The total air volume in the bladder consists of the volume in the uncollapsed portion of the bladder prior to air injection of about 50 ul plus the injected volume of 50–100 ul. The air volume of the bladder is therefore about 125 ul. The total volume of air in the bladder defines the brain tissue pushed aside and is correlated to the trauma imposed upon the brain.

The partially filled bladder assumes a flattened shape when positioned in the brain. If the area of the flattened bladder is described as (x)(y) and the movement of opposite walls of the bladder described as z, then z=the volume change divided by the area or $(V_1-V_2) \div (x)(y)$. Z decreases as (x)(y) increases. The flat partially filled bladder used by the Spiegelberg device limits bladder movement by using a (x)(y) value such that z falls within the brain's ability to move.

The percentage the bladder must be underfilled to function in brain defines the absolute size of the bladder, the bladder surface area and in turn, the rate at which air is lost by diffusion. Air loss defines the system's operating life, i.e., the time the bladder can function before air lost by diffusion must be replaced. The fact that the Spiegelberg bladder must be substantially underfilled to function increases surface area and decreases operating life. The operating life of the Spiegelberg device is further reduced by the relatively inefficient type of bladder used. The Spiegelberg device uses a sleeve-like bladder open at both ends. The bladder is placed along the axis of the catheter body and the bladder ends joined to the catheter. The sleeve-like bladder used is relatively inefficient for several reasons. First, the presence of the catheter body within the bladder reduces the bladder's usable air volume. Second, as the bladder nears exhaustion, the catheter body holds the opposing walls of the bladder apart in a tent-like fashion and renders part of the bladder volume useless. Both effects reduce collapsing efficiency and thereby reduce operating life.

Operating life is also decreased by an additional effect of the large gas volume in the air line that connects the bladder with the bedside transducer. The volume, essentially dead space, accounts for 80% of the bladder volume change required to respond to intracranial pressure fluctuations. Hereinafter, the change in bladder volume caused by pressure change will be referred to as the stroke of the bladder and can be visualized as the z component of (x)(y)(z) in the previously discussed formulae. The stroke of the bladder would be reduced by 80% if the dead space component of the air line could be eliminated from total system volume. A smaller stroke, i.e. a smaller delta z value, would allow the bladder to use more of the bladder air before z=0. A reduction in dead space would thereby increase operating life by reducing bladder stroke. Spiegelberg deals with the limited operating life of the bladder by use of an electromechanical pump that deflates and inflates the bladder at hourly intervals.

The use of a pump to vent and replace air in the bladder on an hourly basis provides another function, that of purging water vapor from the system. The water vapor diffusing into the bladder over the days or weeks that an ICP catheter may be in service can be substantial. If the air in the bladder becomes saturated with water vapor, the regular pulsing of the bladder will cause water vapor to condense and accumulate in the bladder. The condensate will at some time enter the catheter lumen, impede the flow of air and distort the pressure reading. The pump of the Spiegelberg system neutralizes the effect of water diffusion by flushing the bladder each hour with room air, thereby replacing moist air with dry air.

Two deficiencies of the prior art have thus far been explored. First, the volume of air required by a bladder in a system with a long air line displaces an undesirable volume of brain tissue. Second, the egress of air and the ingress of water through the bladder wall are such that an electromechanical pump must be used to exchange and replace air on an hourly basis.

The prior art does not teach a means to lessen brain trauma by reducing non-bladder air volume in an ICP catheter to enable use of a small volume bladder. It particularly does not teach a construction wherein the air volume in the bladder can be limited to 35 ul or less and wherein such a small bladder can operate for more than an 8–12 hour nursing shift.

The prior art does hot teach a system wherein a bladder can function in brain tissue when filled to +50% of its potential volume. The Bobo 007 patent shows a long catheter with significant dead space. The bladder resides in a normal ventricle filled with cerebral spinal fluid (CSF). It will not work if surrounded by brain tissue. The prior art catheter currently marketed by Spiegelberg Gmbh uses a large bladder that is filled to about 25% of its potential volume. It cannot measure ICP if fully filled. The +50% filled bladder of the present invention incorporates more air for a given bladder size and proportionally extends operating life.

No prior art device describes a tip-mounted bladder capable of operating in brain tissue. The prior art does not teach the use of a stent to preserve the elongated shape of a tip-mounted bladder as it enters brain tissue so it does not fold back over itself. It furthermore does not teach the use of a stent with a small cross section to minimize loss of useable air volume. Bobo 007 discloses a flaccid bladder mounted on the distal tip of the catheter that does not employ a stent. The bladder in 007 is used to measure pressure in body spaces wherein the bladder is immersed in liquid such as blood. Such a fluid permits free movement of the bladder and allows the bladder to assume its natural elongated shape without the assistance of an internal support element.

As regards extending operating life by reducing water ingress and air loss, no prior art device teaches constructing the bladder of an air-based catheter from rubber rather than plastic. Rubber, as used herein, refers to materials such as buna N, neoprene, butyl nitrile and butyl rubber. Rubber materials have extraordinarily low water permeability qualities, especially butyl rubber. For example, the water permeability of butyl rubber is $\frac{1}{200}$ that of polyurethane, the base material used in the Spiegelberg device. A butyl rubber bladder essentially blocks water ingress to the extent that a bladder can operate for extended periods without the need to purge humid air. Furthermore, prior art does not teach using an ultra thin butyl bladder to reduce air loss as a means of extending operating life while preserving pressure response. The Bobo 007 patent teaches the use of a variety of plastic materials including polyvinyl chloride, polyurethane, polyvinylidene and combinations thereof but does not teach the use of rubber in constructing a bladder. The use of butyl rubber vs. polyurethane significantly reduces air lost by diffusion. The extended life made possible by the use of a thin butyl membrane plays a critical role in feasibility of substituting a manual pump for the electromechanical pump now used None of the prior art ICP devices separate the functions of pressure measurement and CSF drainage. The separation of functions allows measurement of ICP with a minimally invasive sensor prior to insertion of a more invasive CSF drainage catheter if drainage is required. The prior art system that can both measure pressure and drain CSF requires placement of a catheter in a ventricle deep within the brain at the onset of the procedure.

It is common practice to drain cerebral spinal fluid (CSF) to relieve pressure if the patient's ICP exceeds 20 mmHg. The decision to drain CSF is based solely on whether or not the ICP is elevated. The existing art provides two options to care for a patient. The first option is minimally invasive. It can measure ICP but cannot drain CSF. The second option is more invasive and can both measure ICP and drain CSF. The first option involves placing a 3–5 Fr pressure sensor 1 cm deep into the brain. It has no drainage capability. This approach is good if ICP remains below 20 mmHg and drainage is not required, as it is minimally invasive. It is not good if ICP is elevated and drainage is required in that a second hole must be drilled in the skull to place a ventricular catheter in the brain. The second option involves placing a single lumen 9–10 Fr ventricular catheter into a ventricle located 6 cm deep within the brain. The catheter lumen is attached to a water filled line, which in turn is attached to an external pressure transducer that registers ICP. The water filled lumen can be used to drain CSF if ICP becomes elevated. This approach is good if drainage is required in that the drainage function is immediately available and only one hole need be drilled in the skull. It is not good if drainage of CSF is not required in that it is a more invasive way to monitor ICP than the first option. Presently used systems present a dilemma in that either option could subject the patient to unnecessary trauma. No prior art device provides the ability to look at ICP with a minimally invasive monitor as a first step and then, if need be, introduce a drainage catheter as a second step.

None of the prior art describes a bolt wherein the angle of entry of a drainage catheter can be varied over a wide range to target a ventricle not aligned with the axis of the bolt.

None of the prior art devices provide for the replacement of a clogged drainage catheter with a new catheter in a manner that reduces the risk of infection. Hospital protocol recommends against replacing a clogged drainage catheter with a new catheter in a currently used site due to the risk of infection. Protocol recommends that catheter replacement be done in a fresh site through a new hole in the patient's skull.

None of the prior art devices explicitly address the risk of infection of bolt-mounted catheters. The literature reports that patients served by bolt-mounted catheters have a 4% chance of infection compared to 1% for patients served by a catheter tunneled beneath the scalp for several inches after it exits the drill hole. Prior art bolts do not provide an explicit means of intercepting bacteria en route to the drill hole nor provide a means of discouraging bacteria movement down the drill hole.

Co-pending patent application Ser. No. 09/379,282 by Bobo teaches mounting the transducer on a bolt affixed to the skull. Mounting the transducer proximal to the patient reduces the dead space volume at least an order of magnitude compared to the prior art system wherein the catheter uses a long air line to connect the catheter bladder to a bedside instrument. In the case of a catheter mounted in a bolt, the reduction in dead space reduces bladder wall movement to the extent that a nearly fully filled bladder can be used to measure ICP. In contrast, the dead space of Spiegelberg's long air line requires that a substantially underfilled bladder be used to form an X-Y planar area large enough to make movement in the z dimension compatible with brain tissue.

Although the bladder of a bolt-mounted catheter can operate in a nearly fully filled condition, it would be impractical to design a device that will inject precisely the right amount of air to fully shape the bladder at 0 mmHg STP. The four reasons that prevent precise filling are listed in the order of their impact:

1. The residual air in the bladder before injection varies with how high the ICP is; more squeeze=less air in the bladder=more room for injected air. The maximum injected volume varies with ICP.
2. The temperature of the patient will affect $V_1$ and $V_2$ in the equation $P_1V_1/T_1 = P_2V_2/T_2$.
3. The $CO_2$ level in the brain tissue will result in an initial ingress of gas since $CO_2$ diffuses in more rapidly than other gases present diffuse out.
4. The dimensions of the bladder cannot be precisely controlled. Therefore, the air injector must be designed to comprehend dimension tolerances.

None of prior art devices explicitly address the potential reading error caused by brain tissue as it resists dissection by an inserted bladder. At pressures under approximately 20 mmHg, the pressure inside the bladder is a composite of the intracranial pressure (ICP) and the resistance of the brain tissue surrounding the bladder to be dissected by the bladder. The dissection pressure component rises inversely with ICP and directly as the percentage inflation of the bladder with air increases. So, the lower the ICP and higher the percentage inflation, the greater the error. At some point, around 20 mmHg, the pressure in the bladder is such that it completely pushes aside brain tissue, at which time the dissection component is insignificant. In order to provide very accurate readings throughout the 0–20 mmHg range, the system is equipped with a modification that dissects the brain tissue in which the bladder will reside. The dissection component of the ICP reading is thereby rendered insignificant and the accuracy of the reading is preserved throughout the range. The inventors are unaware of any published information on the Spiegelberg device related to dissecting brain tissue. The device presumably employs some algorithm to determine exactly how much air should be injected into the bladder for a given ICP. Whether or not brain tissue is dissected by the algorithm and whether or not dissection is a planned or serendipitous event is unknown.

SUMMARY OF THE INVENTION

A first objective of the present invention is to minimize trauma inflicted upon brain tissue by minimizing the air volume required by the bladder of a gas-column catheter. Air volume is minimized by mounting the pressure transducer adjacent the patient. In one version of the present invention, the transducer is directly mounted on a bolt attached to the skull of the patient. In another version, the transducer is attached to the proximal end of a flexible catheter that is as short as possible. The minimal length is achieved by securing the proximal end near the patient's neck or shoulder by adhesive tape or by a gown clip attached to the cable. Mounting the transducer adjacent to the patient greatly reduces the dead space in the long air line used in the prior art to connect the bladder to a bedside instrument housing a pressure transducer. Non-bladder volume, essentially dead space, is reduced a factor of approximately 110 in the case of a bolt-mounted transducer and a factor of 11 in the case of the flexible catheter. The reduction in dead space significantly reduces the volume of air required by the bladder to respond to pressure fluctuations by reducing the bladder stroke. A portion of the reduction in required bladder volume is added back to the bladder to assist in achieving a second objective, that of extending the operating life sufficiently to replace an electromechanical pump with a manual pump.

The present invention, including air added to extend operating life, achieves a fourfold net reduction in bladder air volume and a fourfold reduction in brain tissue volume displaced, thereby achieving our first objective of reducing brain trauma.

The second objective of the present invention is the use of the manual pumping system described in Bobo 007 in lieu of the costly electromechanical pump required to support current air column catheters. This objective is of great economic importance in that a manual system eliminates the capital cost of an electromechanical system and thereby eliminates a significant disincentive to adopt an air-based ICP system. From a practical standpoint, it is important that maintenance of a manual system not be unduly burdensome to the nursing staff in terms of the frequency at which air must be replaced. One pumping event per shift would be compatible with the normal hospital protocol of checking proper functioning of a monitoring instrument. Five elements of the present invention contribute to the attainment of a once-per-shift maintenance schedule. Three are derivative of the reduction in dead space. First, the reduction in dead space reduces gas loss by diffusion by enabling the use of a small bladder with a correspondingly small surface area. Second, the reduced stroke of the bladder allows the bladder function in a more fully depleted state at end of its operating life. The smaller delta z extends the time before z=0. Third, the reduction in wall motion allows the bladder to function in brain tissue when filled to +50% of its potential volume vs. 25% as in the case in the prior art. The additional air volume extends operating life. The short flexible catheter function is filled to +50%. It functions in a partially filled state to decrease movement in the z dimension and thereby deal with the increase in dead space. The lesser air volume in the bladder of a flexible catheter results in a somewhat shorter operating life, but one consistent with the desired life of a bladder using a manual pump. Two other elements affect operating life. The sleeve bladder now used is replaced with a more efficient tip-mounted bladder, which allows the bladder to use more of the available air. Finally, use of a butyl rubber bladder extends operating life by reducing air loss by diffusion and preventing the ingress of water. The extension in operating life due to the combined effect of the five elements make it practical to replace an electromechanical pump with a manual pump.

A third objective of the present invention is to provide a bolt that allows a doctor to insert a small probe into the brain to measure ICP and then, if ICP is elevated, to insert a drainage catheter into a ventricle through a separate passageway in the bolt.

A fourth objective of the present invention is to provide a bolt-based system that allows the drainage catheter to be introduced into the brain at such an angle as may be required to target a ventricle. Since the hole drilled in the skull is done by a hand-held drill, the trajectory of the drill is not well controlled. Therefore, the bolt's axis may or may not be aligned with a ventricle. Furthermore, the target ventricle may shift laterally toward or away from the midline of the skull as a result of trauma. Should it be necessary to insert a drainage catheter, the doctor must be able to vary the entry angle of the catheter in relation to the axis of the bolt to properly target the ventricle. The present invention allows the doctor to introduce a drainage catheter into an off-axis ventricle by passing the catheter through the bolt at the necessary angle.

A fifth objective of the present invention is to allow the doctor to replace a clogged drainage catheter without undue risk of infection: The infection risk of current devices is such that replacement catheters must be placed in a new hole drilled in the skull. The catheter passageway in the present invention is lined with a removable insert that incorporates all surfaces that might become contaminated. The insert is removed when the clogged catheter is removed thereby removing the contaminated surface and reestablishing a sterile field to allow the replacement of a clogged catheter without undue risk of infection.

A sixth-objective of the present invention is to reduce, the risk of infection by establishing a physical and chemical barrier to the ingress of bacteria between the surfaces of a bolt and a skull drill hole. Bacteria migration is discouraged in one version by attaching the bolt to the skull with a series of radial ribs that physically block the movement of bacteria down the drill hole. Bacteria survival is minimized by applying an antimicrobial agent tothe bolt portion that resides on and in the skull.

Another objective of the improvement in the present invention is to remove the possibility of introducing an error in the pressure reading in the 0–20 mmHg range due to the reluctance of the brain tissue surrounding the bladder to separate. The system is modified to cause that portion of brain tissue within which the bladder will reside to be dissected at the start of the procedure. The dissected section creates a pocket in brain tissue slightly larger than the volume of the bladder in its normal operating mode. A pocket can be created by a manual pump that overfills the bladder so it becomes somewhat larger than its normal operating volume. Alternatively, the pocket can be created by inserting a rod into the part of the brain that will be occupied by the bladder prior to inserting the bladder into the brain.

A corollary object of the improvement in the present invention is to provide a method of preconditioning the tissue by exposing the tissue to the dissecting means for a sufficient time for the tissue to adjust to the presence of the shape: that is, time enough for the tissues that are under load to tear and dissect until the dissection process is complete. The method requires that the overfilled bladder or the dissecting rod remain in place for up to a minute to assure that the brain tissue has fully responded to the dissection process.

In brief, the invention is carried out as follows. The invention addresses the limited ability of brain tissue to move by minimizing V in the expression $P_1V_1=P_2V_2$. $V_1$ and $V_2$ consist of $V_{nb}$=volume of non-bladder air and $V_b$=volume of bladder air. The volume change, $V_1-V_2$, required by the bladder to reflect a pressure change is reduced by minimizing $V_{nb}$. $V_{nb}$ is minimized by attaching a pressure transducer close to the patient's skull such as by directly coupling it to a bolt affixed to the skull. The invention greatly reduces the dead space in the long air line between the catheter and pressure transducer used in prior art. The reduction in dead space provides a number of benefits. First, it reduces brain trauma by reducing the air volume required by the bladder to reflect pressure change. Second, it improves three parameters that affect operating life. Operating life is defined as the period of time the bladder can operate before air lost by diffusion must be replaced. The three parameters are surface area, bladder stroke and the extent to which the bladder that can be filled with air and still function in brain tissue. The improvement in operating life is sufficient to allow the use of a manual pump in place of the presently used electromechanical pump.

The surface area through which water enters and gas is lost decreases as bladder volume decreases. The surface area of the bladder used in the present invention is ⅕ the surface area of the prior art bladder design now used. Water ingress and gas egress is therefore reduced by a factor of five.

Bladder stroke, i.e., the change in bladder volume, $V_1-V_2$ that accompanies a change in pressure is reduced as dead space is reduced. For example, in order to respond to a waveform with a 10-mmHg pulse pressure, the bladder stroke of the bolt mounted transducer is 1.4% vs. 6.0% for the partially inflated bladder of the prior art. The reduction in stroke volume allows the bladder to function when the air volume is more nearly depleted thereby extending the operating life of the bladder.

Minimizing dead space reduces bladder wall motion such that the bladder can function when the bladder to be more fully filled. The prior art bladder is filled to ~25% of its potential. In contrast, the bladder of the bolt version and flexible catheter version can be filled to +80% and +50% respectively. The additional air extends life. The present invention further extends operating life by the use of two other elements.

The first element is the use of a bladder with more efficient collapsing characteristics. The second element is the use of a butyl rubber bladder. The prior art bladder is open at both ends and mounted on the catheter in a sleeve-like fashion. The bladder used in the present invention is closed at one end and open on the other. The open end is placed on the tip of the catheter. The tip-mounted bladder is able to collapse more completely than a sleeve mounted bladder and adds significantly to the operating life. A small diameter support element within the tip-mounted bladder allows the bladder to pass into the brain without folding over yet detracts little from the air volume available within the bladder.

The use of butyl reduces air loss by a factor of 5 vis a vis the prior art and limits water vapor ingress to the extent that the device can operate for the required monitoring period without risk of water condensate interfering with air movement between the bladder and transducer.

The five elements discussed make it possible for the bladder to operate for more than a nursing shift even though the gas volume is ¼ to ⅕ that of the prior art. The present invention thereby makes it possible to substitute a manual pump for the electromechanical pump now used.

The invention covers three bolt-based systems and one flexible catheter system. Two bolt systems measure pressure in parenchymal brain tissue. A third system has the ability to measure ICP and to provide a passageway for the introduction of a drainage catheter into a ventricle. The three bolt systems are secured to the skull in a drill hole. The fourth system is a flexible catheter than can be used in conjunction with cranial operations where a flexible catheter is more easily placed than a bolt. The bolt systems will be discussed first.

The intraparenchymal system can be made in two versions. In one version, the catheter is integrated into a bolt and introduced into the brain as the bolt is placed in the drill hole. In another version, the catheter assembly and bolt are separate entities. The catheter is inserted into the bolt after the bolt is attached to the skull. The bladder in either case enters the brain to a depth of about 1 cm.

In the ventricular system, the catheter and bolt are integrated. The catheter enters the brain when the bolt is attached to the skull. The ventricular bolt provides a dedicated passageway through which the doctor can place a ventricular catheter if drainage is indicated at any time during the patient's care. Thus, it is a dual function device that measures pressure with a minimally invasive pressure sensor and then provides a pathway through which a more invasive drainage catheter can be inserted if ICP is elevated. The system thereby allows the doctor to match the invasiveness of the procedure with the need of the patient. The passageway of the bolt is designed to allow the doctor to introduce a catheter at an angle to the axis of the bolt of about 15 degrees. The flexible angle of entry enables the doctor to enter a ventricle offset from the axis of the bolt. The ventricular bolt can be modified to provide a second port to allow insertion of a sensor into the brain that monitors a parameter other than pressure.

The bolt systems employ several features to reduce the risk of infection. In one version of the present invention, the screw conventionally used to attach the bolt to the skull is replaced with a series of radial ribs made of a deformable material. The bolt is tapped into the drill hole with a mallet. Interference between the ribs and the drill hole holds the bolt firmly to the skull. The ribs constitute a series of radial barriers that act as barriers to the migration of bacteria. In contrast, a conventional screw-in bolt provides a spiral pathway down which bacteria can migrate from the scalp to the brain if the monitoring period is prolonged. The invention further reduces the risk of infection by providing features in the product that apply an antimicrobial agent to the skull and to the drill hole. The features further act as a reservoir for the agent to provide continuing protection over time. The risk of infection is a serious issue as attested to by the fact that many doctors refuse to measure ICP due to risk of infection. The antimicrobial applicator and reservoir aspects are therefore important characteristics of the invention. The literature reports that the risk of infection of a bolt system is 4 times that of a non-bolt system wherein the catheter is tunneled beneath the scalp for a 3–5 cm after it exits the drill hole. The data concerning infection risk of a bolt system vs. a tunneled catheter underlines the merit of incorporating antimicrobial features into a bolt system.

BRIEF DESCRIPTION OF THE DRAWINGS

These and other details of the invention will be described in connection with the accompanying drawings, which are furnished only by way of illustration and not in limitation of the invention, and in which drawings:

FIG. 1 is a perspective view of a fully assembled intraparenchymal pressure system showing an intraparenchymal bolt mounted in the skull, a pressure coupling catheter assembly that resides in the bolt and extends into the brain and a transducer assembly that couples to the catheter;

FIG. 2 is an exploded view of the assembly in FIG. 1;

FIG. 3 is cross sectional view of each element of the assembly of FIG. 1;

FIG. 3a is an enlarged cross section view of the bottom portion of the transducer assembly;

FIG. 3b is an enlarged cross section view of the bottom portion of the bolt assembly showing alternative grooved gasket on the left and non-woven gasket on the right;

FIGS. 3c–3e are enlarged cross-section views of the bottom portion of the catheter assembly;

FIG. 4 is a partially exploded view of a second version of a intraparenchymal pressure system showing a bolt that is screwed into the skull and a separate pressure coupling catheter that is inserted into the brain through the bolt and locked to the bolt;

FIG. 4a is a cross section view of the bolt particularly showing the locking groove used to secure the catheter to the bolt;

FIG. 4b is an elevational cross-section view of the combination pump and holder tool with the holder end facing down to mount on the piston;

FIG. 4c is an elevational cross-section view of the combination pump and holder tool with the holder end mounted on the piston;

FIG. 4d is an elevational cross-section view of the combination pump and holder tool with the pump end mounted on the piston;

FIG. 4e is an elevational cross-section view of the transducer fully seated on the piston;

FIG. 5 is a partially exploded view of a ventricular bolt assembly showing the bolt, catheter and drainage catheter;

FIG. 5a is plan view of the bolt without a temporary cap;

FIG. 5b is a partially exploded cross section view of a ventricular bolt with a temporary cap;

FIG. 5c is a cross section of the ventricular bolt body showing an access port for an additional sensor.

FIG. 5d is a cross section of the ventricular bolt body showing a second access port for an additional sensor;

FIG. 8 is a perspective view of a short flexible catheter positioned in the brain, secured to the body and attached to a transducer housing; and FIGS. 8a–b show the placement of the o-ring groove on the piston used for the bolt and catheter that defines the volume of air injected.

BEST MODE FOR CARRYING OUT THE INVENTION

Figure 4F:
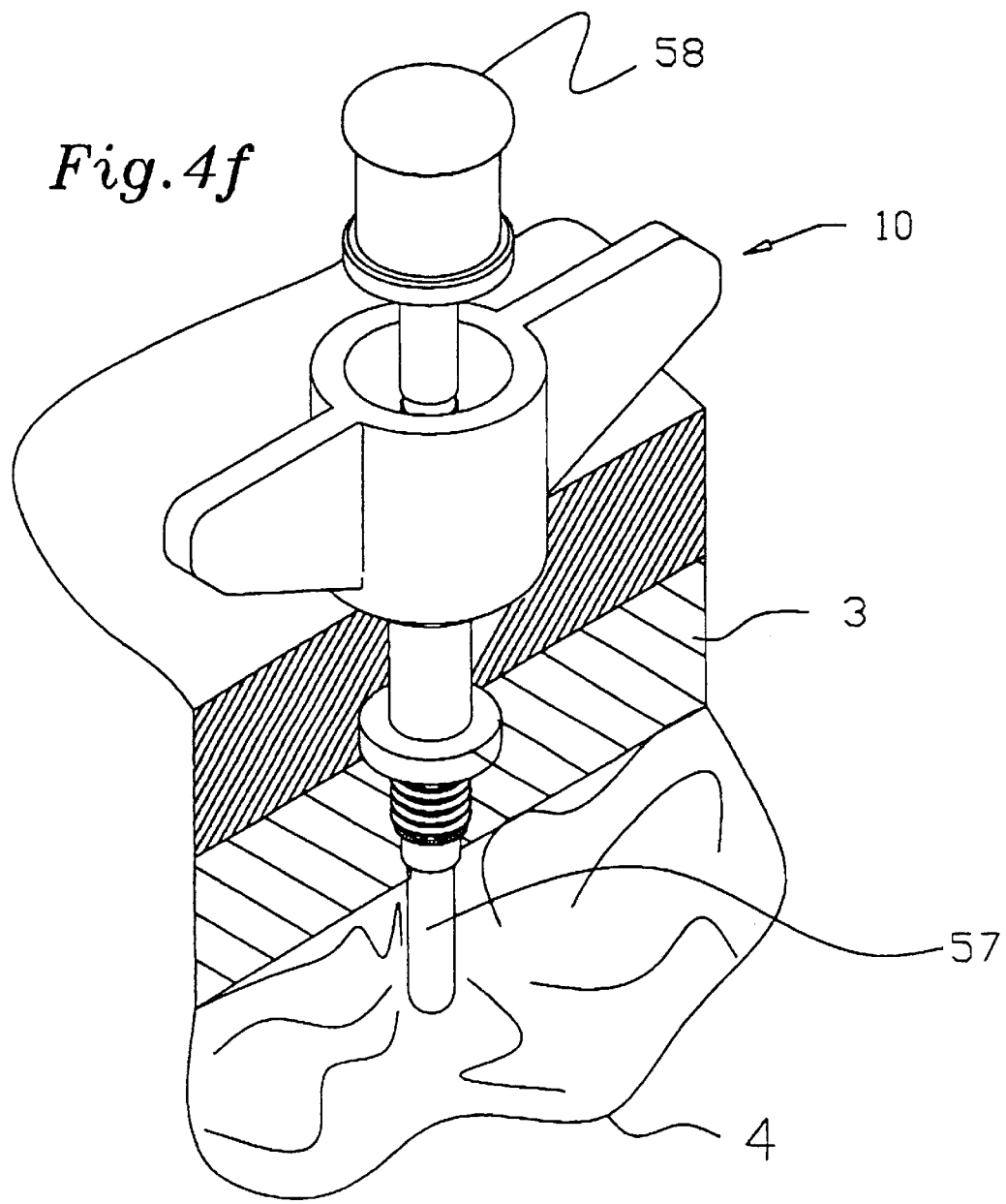
FIG. 4f is an elevational cross-section view of a dissecting rod partially inserted into the bolt and brain.

The present invention is an intracranial pressure (ICP) monitoring system. A first version of an intraparenchymal system 1 is depicted in FIGS. 1 and 2. It consists of three subassemblies: an IP bolt 10, a pressure coupling assembly 6 fixed within the bolt and a transducer assembly 7. The bolt is fixed in a drill hole 2 of a skull 3. The distal end of the pressure coupling assembly is a bladder 20 made of a flaccid material. It resides in a brain 4 when the bolt is set in the skull. The volume of the bladder changes according to $P_1V_1 = P_2V_2$. The pressure within pressure coupling assembly thereby mirrors the pressure of the brain. The proximal end of a capillary tube lumen 24 terminates in a piston 12. As shown in FIGS. 3–3a, the piston is designed to engage a cylinder 43 within a housing probe 42. As the housing probe is inserted into a probe well 11, the cylinder engages the piston. A seal 45 creates a closed system between the cylinder and piston. The cylinder communicates with a pressure transducer 41 via a connecting lumen 44. The transducer translates the pressure signal conveyed by the coupling assembly into an electrical signal. The signal is transmitted to a patient monitor as is well known in the art.

In this version, the pressure coupling assembly is incorporated into the bolt by insert molding or adhesive bonding. As shown in FIGS. 3 and 3b, the distal end of the intraparenchymal (IP) bolt 10 terminates in a rib set 17. The bolt is pushed into a drill hole 2 in a skull 3. The ribs used to secure the bolt within the drill hole are larger in diameter than the drill hole and made of a deformable material such as polycarbonate. When the bolt is pressed into the drill hole, the interference between the ribs and the skull deforms the ribs and secures the bolt in place. Since the bolt and the pressure coupling assembly are joined to form a single part, it is not appropriate to terminate this version with a threaded section as a screw-in bolt would cause the bladder 20 to wrap around itself during installation and make the bladder dysfunctional.

As shown in FIG. 3, a skull gasket 13 is placed beneath a bolt shoulder 18. The bottom of the gasket contacts the skull. As shown in left alternative FIG. 3b, the gasket may have a gasket groove 14 filled with an antimicrobial agent 19. Alternatively, as shown in right alternative FIG. 3b, the gasket may be a homogeneous gasket such as a non-woven skull gasket 15 impregnated with an antimicrobial agent or a material composed of a silver ion emitting material. The gasket acts as a means of applying the agent to the skull and serves as a reservoir of agent that elutes into the adjacent tissue bed over time. The series of ribs compressed against the bone act as a series of barriers and discourage migration of bacteria down the drill hole. As a further barrier to ingress of bacteria, an antimicrobial agent 19 is applied to between the ribs. The rib set then acts as an applicator that applies agent to bone and serves as a reservoir of agent that elutes into the adjacent tissue bed over time. Alternatively, the exterior of the ribbed section can be coated with a silver ion emitting material.

The various elements of the coupler assembly 6 are shown in FIGS. 3 and 3c–e. The bladder 20 is fixed to the distal end of a plastic sleeve 22 mounted on a capillary tube 23. The proximal end of the capillary tube is bonded into a piston 12. The distal end of the tube extends into the bladder to form a stent 21 as shown in FIGS. 3c–3e. The stent prevents the bladder from folding over as it enters brain tissue. A protective guard such as a rounded tip 25 is affixed to the end of the stent to keep the stent from puncturing the wall of the bladder. In FIG. 3d, the stent is comprised of a U-shaped wire anchored in the plastic sleeve. In the FIG. 3e, the capillary tube extends into a bladder that has a necked down distal end. The end of the capillary tube is sealed to the bladder. The capillary tube is closed at the distal end and terminated in a sharp tip 27 to allow the device to be into resistive tissue other than the brain. As shown in FIGS. 3c and 3e, the capillary tube wall is penetrated by a multiplicity of a stent hole 26 that allows air to move in and out of the capillary tube lumen 24 as, required The details of the transducer assembly 7 are shown in FIG. 3. A pressure transducer 41 is mounted in a housing 40. The pressure signal generated by the transducer is conveyed by a cable 46 to a patient monitor, which displays pressure as a number and waveform as is well known in the art. The act of joining a housing probe 42 to the piston 12 causes a bolus of air to be injected into the bladder and effectively actuates the bladder.

FIG. 4 shows a second version of an intraparenchymal system wherein an IP bolt 10 and the pressure coupling assembly 6 are separate elements. In this version, the bolt may be attached to the skull by a bolt screw 16 or a series of ribs as described in the first version. If a bolt screw is used, a bolt wing 31 is placed on a bolt body 30 to provide the leverage required for screwing the bolt into the skull. After the bolt is in place in the skull, the pressure coupling assembly is inserted into a bolt cavity 32 until a locking ring 33, such as an o-ring engages a locking groove 34 shown in 4a. The locking ring permanently joins the bolt and pressure coupling assembly.

FIGS. 4b–4d show a procedure tool 50 positioned over the pressure coupling assembly 6. A holder sleeve 51 has an interior vented receiving chamber 52 having an air vent 53 which releases the air as the holder sleeve 51 engages the seal 45 of the piston 12, thereby enabling the tool to be used as a holder to assist in placing the pressure coupling assembly into the bolt 10. The tool has an interior partition 56 in the tool, which separates the holder chamber from a pump sleeve 54 having an airtight receiving chamber 55. The chamber fits slidably over the seal 45. Upon fully mounting the chamber on the piston 12, a quantity of air is injected into the bladder. The air volume causes the brain tissue in contact with the bladder to dissect and in essence create a pocket for the bladder. The quantity of air injected is larger than that injected in normal operation when the housing probe is placed on the piston to activate the bladder. The larger volume insures that the pocket formed in the brain will be large enough to preclude undissected brain tissue adding a pressure component in the ICP reading.

FIG. 4e shows the final position of the housing probe 42 on the piston 12. It can be seen in FIG. 4d that the stroke length of the receiving chamber 55 is greater than that of the probe 42 shown in FIG. 4e. The air volume injected by the receiving chamber is proportionally larger.

FIG. 4f shows a dissecting rod 58 partially inserted into a bolt 10 and into the brain 4. The rod is inserted into the brain until a rod stop contacts the proximal end of the bolt. The rod, when fully inserted, occupies the space in the brain in which the bladder 57 will come to rest. The diameter of the rod is somewhat larger than the bladder 57 of the pressure coupling assembly. The rod dissects the brain tissue and eliminates the possibility of that the ICP reading will be affected by the reluctance of brain tissue to separate.

FIG. 5 shows the elements of a ventricular bolt assembly 8 in combination with the elements of a drainage catheter assembly 9. As shown in FIGS. 5a and 5c, a ventricular bolt 60 consists of a side arm 61 with a probe well 11 and an open passageway comprised of an anchor well 62 positioned above an inner bore 64. In FIG. 5b, a pressure-coupling catheter 6 is integrated into the bolt by bending the capillary tube 23 to conform to the angle of the side arm 61. The proximal end of the assembly, a piston 12, is located in the probe well 11. In operation, the piston and housing probe interact to inject air into the bladder in a manner identical to that previously discussed. The side arm geometry makes it possible to move the pressure measurement function off to one side of the bolt. The capillary tube 23 is positioned into or against the wall of the inner bore so as to preserve as much of the inner bore as possible for passage of a drainage catheter 68. The resultant inner bore provides room for the passage of the drainage catheter 68 at an angle to the axis of up to 15 degrees as seen in FIGS. 5b–c. It will be appreciated that pressure sensors other than an air-column catheter could be incorporated into the ventricular bolt and that the sensor need not be integrated into the bolt. For example, a miniature strain gage sensor could be introduced into the brain through a sensor passageway such as an outer bore 65, shown in FIG. 5d. The bolt in this case would be expressly designed to receive and retain such a sensor. A second sensor such as an oxygen or temperature sensor could introduced into the brain by use of a bolt with a second side arm 61 having its own outer bore 65 as shown in FIG. 5d. In this configuration, the outer bore is being extended beyond the ribbed section of the bolt such that a bore extension 90 enters the brain. The distal end of the outer bore is be capped with and extension cap 91 to allow the sensor to be introduced or removed as needed without breaking sterility. If an oxygen probe is used, the cap can be made of silicone to allow diffusion of oxygen.

Several design characteristics are required to provide the advantages of the ventricular bolt described regardless of the type of the type or number of sensors used or the manner in which the sensors are incorporated into the bolt. Each sensor must be situated off center in the inner bore to preserve the center section of the inner bore for passage of a drainage catheter and the passageway must be large enough to allow the catheter to enter the brain at an angle to the centerline of the passageway.

The drainage catheter assembly, which is shown in FIG. 5, consists of four elements. The catheter is a single lumen drainage catheter 68 with radial holes in the distal section as is well known in the art. It is guided into a target ventricle 5 by means of a guiding stylet 69. Once in the brain, the catheter is secured to the bolt by means of an elastomeric catheter anchor sleeve 71 when a compression cap 70 is screwed onto the threaded section of the anchor well 62. Prior to use, the anchor sleeve and compression cap are strung on the catheter and held in place by friction.

Figure 6:
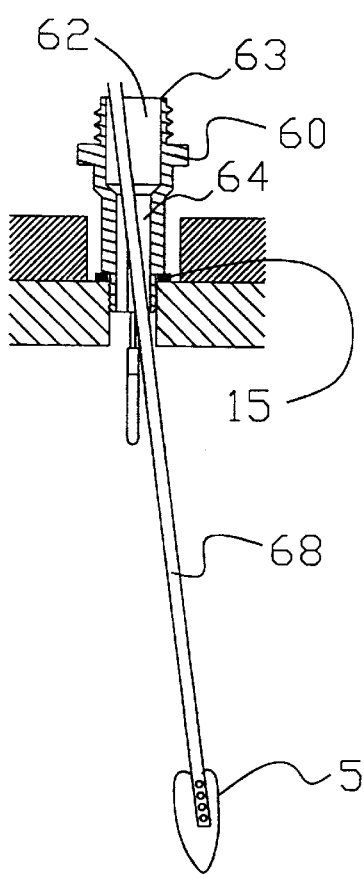
FIG. 6 is a cross section view of a ventricular bolt with a drainage catheter particularly showing the range of movement of the catheter within the bolt.
Figure 7:
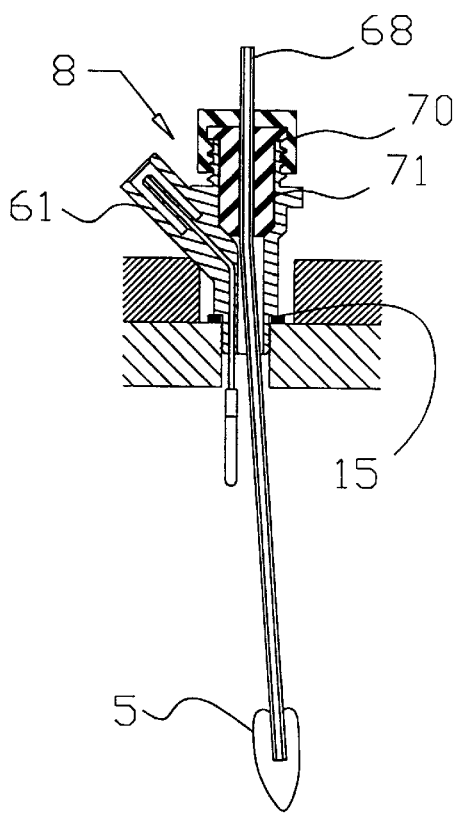
FIG. 7 is a cross section view of the ventricular bolt showing the catheter, anchor sleeve and cap in their final positions.
Figure 7A:
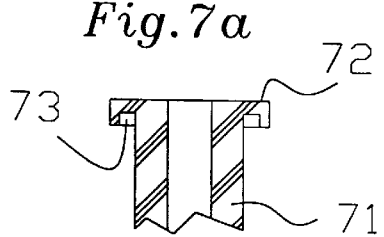
FIG. 7a is a cross section view of the anchor sleeve particularly showing an antimicrobial agent filled groove.

If CSF drainage is required, the temporary cap 66 shown in FIG. 5b is removed from the anchor well and the drainage catheter 68, supported by the stylet 69, is inserted into the brain through the inner bore. As shown in FIG. 6, the open inner bore allows the catheter to enter the brain at an angle up to about 15 degrees from the centerline of the bolt. The diameter of the inner bore, the diameter of the anchor well and the height of the anchor define the entry angle. The maximum entry angle can be varied by varying these dimensions. Once the catheter is positioned in the ventricle 5, the stylet 69 is removed. As shown in FIGS. 7–7a, the sleeve 71 is moved down the catheter and into the anchor well. The compression cap 70 is screwed on to the threaded section of the anchor well and tightened. The resultant compression fixes the catheter within the sleeve and compresses the flange 73 against the well face 63. The compressive force of the anchor sleeve provides a barrier to the ingress of bacteria between the sleeve and the anchor well. A flange groove 73 is provided in the face of the flange 72. The groove is filled with an antimicrobial agent to further discourage bacterial ingress.

If the drainage catheter becomes clogged with tissue or blood, the compression cap 70 is unscrewed and the catheter and anchor sleeve withdrawn from the bolt. A new catheter set, consisting of a drainage catheter 68, a stylet 69, catheter anchor sleeve 71 and a compression cap 70, is inserted into the bolt to replace the clogged catheter. The sterile well face 63 of the bolt is the proximate surface to the catheter's entry path. The sterile condition of the well face is assured by the pressure of the flange against the well face in combination with the antimicrobial agent within the flange. The sterile surface provides protection against contaminating the replacement catheter by inadvertent contact with the well face during insertion.

The bolt is secured to the skull by a rib set 17. The ribs are slightly larger than the drill hole. The ribs are formed of polycarbonate and deform somewhat when the bolt is tapped into the drill hole with a mallet. The resultant mechanical forces securely affix the bolt to the skull. A screw-in bolt is inappropriate in this design due to the eccentric position of the coupling catheter within the inner bore. Rotation of the bolt would cause the catheter to orbit in brain tissue. Although it would be possible to screw in an intermediate part and then affix the bolt to that part, a rib set is preferred for reasons of drill hole size, convenience and to utilize the mechanical barrier properties of a rib set. A skull gasket 13 or 15 is positioned beneath the bolt shoulder and serves the same purpose as the gasket used on the intraparenchymal bolt.

FIG. 8 shows a flexible catheter 80. The catheter body is tunneled under the scalp for a short distance after it exits the drill hole and continues down to the shoulder where it is secured by an adhesive patch. The proximal end terminates in a piston 12. The piston is connected to a housing probe 42 to inject the air required to activate the bladder in the manner previously described.

The invention described addresses each of the objectives set forth earlier. One objective is to reduce the size of the air bladder in order to reduce brain trauma. A second objective is to substitute a manual pump for the costly electromechanical pump presently used to replace air lost through the bladder wall by diffusion and to flush water vapor from the bladder.

An air-based catheter operates on the principle set forth in Boyle's law of $P_1V_1=P_2V_2$. Boyle's law dictates that a change in pressure results in a comparable change in the volume of the system. The change in the system volume required by a change in pressure is accomplished by a change in the volume of a flaccid bladder mounted on the catheter. The measurement of pressure in brain tissue by an air-based catheter is difficult, however, in that brain tissue is limited in its ability to move to compress or expand the bladder volume. A functional design, therefore, must limit the movement required of the bladder wall so that it does not exceed the brain tissue's ability to move.

One version of the present invention connects a transducer to a catheter insert molded into a bolt as shown in FIG. 1. In a second version of the invention, shown in FIG. 4, the catheter is a separate entity that is placed in a bolt after the bolt is affixed to the skull. Attachment of the transducer to the bolt results in a dramatic reduction in non-bladder volume by essentially eliminating the long air line of the prior art that runs between the bladder and a bedside instrument. The air line volume is essentially dead space that requires a proportionally increase in bladder volume to satisfy $P_1V_1=P_2V_2$. In this version of the invention, as shown in FIG. 3, Vnb consists of the volume of a short connecting lumen 44 plus the air volume in the capillary tube. Placement of the transducer directly on the patient reduces non-bladder volume from the 550 ul volume of the Spiegelberg system to 5 ul in the present invention. In a third version of the invention, shown in FIG. 5, a center passageway is provided to allow placement of a drainage catheter if needed. The dead space of this version is also 5 ul. A fourth version, shown in FIG. 8, addresses procedures wherein a flexible catheter is more appropriate than a skull-mounted bolt. In this version, the transducer is connected to a flexible catheter that is as short as possible. The proximal end of the catheter is secured to the patient's shoulder or neck area by an adhesive patch or a gown clip attached to the transducer cable. In this version, the dead space volume is 50 ul vs. 550 ul for the Spiegelberg catheter.

The concept of placing the transducer adjacent to the patient provides a dramatic reduction in the non-bladder volume of an air-based catheter system. It reduces non-bladder volume by a factor of 110 in the bolt version and a factor of 11 in the flexible catheter version. The useable air volume in the bladder of the present invention is ~20 ul, a quantity of air sufficient to provide an operating life in excess of 12 hours. The reduction in usable air volume in the bladder from 50–100 ul in the prior art to 20 ul represents about a four-fold reduction and satisfies the first objective, that of reducing brain trauma by reducing bladder volume.

The reduction in dead space also contributes to the second objective, that of extending operating life sufficiently to use a manual pump. It is achieved in large part by a reduction in dead space. The reduction in dead space air extends operating life in three ways. First, it allows a smaller bladder to satisfy the requirements of $P_1V_1=P_2V_2$. The reduced surface area of the smaller bladder reduces diffusion losses by a factor of five. Second, the stroke required by the bladder to reflect pressure change is reduced. Stroke can be visualized as the movement of the xy planar area of the bladder wall in the Z direction. The reduction in delta z allows the bladder to operate for a longer period until the opposing walls contact and z=0. Third, the reduction in bladder wall motion is such that the bladder can be +80% filled in the case of a bolt version or more than 50% filled bladder in the case of a flexible catheter version. The ability to more fully fill the bladder improves operating life by allowing a bladder of a given surface area to carry more air.

In summary, reduction in the dead volume of the lumen connecting the bladder and transducer reduces brain trauma by reducing the volume of air required by the bladder. The reduction in bladder size extends operating life by reducing the surface area thereby reducing diffusion of gas through the bladder. The reduced dead volume reduces the stroke of the bladder thereby increasing the extent to which the bladder can be depleted. It also enables the use of a more fully filled bladder thereby making increasing useable air volume.

The effect of mounting the transducer directly on a bolt attached to the patient is quantified in the table 1. A comparison of key parameters of the bolt and flexible catheter system is presented in table 2. Potential volume is the volume of the bladder when fully filled. Residual air is the volume of air in the bladder when the catheter is in the brain and the lumen open to the atmosphere. Injected air is the air inserted into the system by a pumping event. The air replacement interval is the manufacturer's recommendation concerning venting and refilling the bladder.

TABLE 1

| | Parameter | Spiegelberg | Present Invention |
|---|---|---|---|
| 1 | Air lumen length = air line + catheter | 154 cm | 5 cm |
| 2 | Lumen diameter required to convey signal | 0.75 mm | 0.3 mm |
| 3 | Air in catheter lumen and air line (dead space) | 550 ul | 5 ul |
| 4 | Bladder-potential volume[1] | 425 ul | 31 ul |
| 5 | Bladder-residual volume[2] | ~25–50 ul | 3–5 ul |
| 6 | Injected volume | 50–100 ul[3] | 20 ul |
| 7 | Total air volume in bladder[4] | ~100–125 ul | ~25 ul |
| 8 | Total air volume in the system | 625–650 ul | ~33 ul |
| 9 | Injected air as a % of system volume | 8–15% | 60% |
| 10 | Bladder volume/system volume | ~20% | 85% |
| 11 | Dead space as a % of total | +80% | 15% |
| 12 | Bladder volume change required to respond to a 10 mmHg pressure change | ~8% | 1.6% |
| 13 | Ratio of wall movement in mm. Spiegelberg = 1 | 1 | <1/2 |

TABLE 1-continued

| Parameter | Spiegelberg | Present Invention |
|---|---|---|
| 14 Bladder area | 3.4 sq. cm | .7 sq. cm |
| 15 Air replacement interval | 1/hour | 1/20+ hrs |

[1]Net of catheter or stent within bladder
[2]Residual varies with ICP collapsing pressure.
[3]Injected air varies according to the ICP pressure encountered
[4]Sum of the residual air in bladder prior to air injection plus injected air Mounting the transducer directly to the bolt reduces the length of the air lumen between the bladder and the transducer by a factor of 30. The short lumen makes it possible to reduce the diameter of the catheter lumen and still preserve frequency response. The combination of the smaller diameter and shorter length results in a 110-fold reduction in the volume outside the bladder. As shown in the above table, the reduction in dead space allows the use of a smaller fully filled bladder that increase the bladder volume as a percent of system volume from 15% to 85%.

It has been found that the brain can provide the movement required to contract and expand as required by a changing bladder volume if the bladder volume of the several embodiments of the present invention described if the bladder volume represents approximately 50% or more of the total system volume. The preferred system design is one wherein the bladder volume is larger than the minimum required. The additional air extends the operating life of the system. Accordingly, the preferred design of the bolt system is one in which the initial bladder volume represents 66% or more of the total system volume such as the 85% version described in table 1.

In some neurosurgery procedures, it is desirable to use a flexible catheter rather than a bolt. A flexible catheter 80 is shown in FIG. 8. The bladder is activated by connecting the catheter to the transducer housing in the same manner as the bolt version. Dead space is minimized by using the minimum catheter length possible. As a practical matter, the transducer and catheter need to be secured to the body so an inadvertent tug on the transducer cable will not pull the catheter out of the brain. A catheter 45 cm long provides enough length to traverse from the head to the patient's neck or shoulder. The catheter is anchored to the patient's neck or shoulder by an adhesive patch or a gown clip attached to the cable. The dead volume added by the length of the catheter reduces the ratio of (bladder volume)÷(system volume) to 30%. The bladder in this embodiment is filled to about half of its capacity to allow it to flatten somewhat in the brain. The sides of the oval formed by the walls of a partially filled bladder act as two planes that limit bladder movement in the z direction as explained in the Spiegelberg construction.

The bladder used for the flexible catheter is the same one used for the bolt catheter. The injection volume of the flexible catheter is reduced by lowering the o-ring location on the piston. FIG. 8*a* shows the position of the o-ring on the bolt piston and 8*b* shows the lower position on the catheter piston. Varying the o-ring position allows one transducer to serve either a bolt or a catheter device and thereby simplifies hospital logistics.

The operating life of the catheter bladder is less than that of the bolt bladder in that the volume of air injected during a pumping event is less and the volume of air required to function at end of life is greater since the stroke is greater.

The cumulative effect of the various elements of the present invention are such that the operating life still meets the once per shift maintenance objective set forth. The parameters of each system as shown in table 2.

TABLE 2

| Parameter | Bolt mounted catheter | Flexible catheter |
|---|---|---|
| Bladder-potential volume[1] | 31 ul | 31 ul |
| Bladder-residual volume[2] | 3–5 ul | 3–5 ul |
| Injected volume (usable volume) | 20 ul | 17 ul |
| Total air volume in bladder | 28 | 25 |
| Dead space volume ul | 5 | 52 |
| Total system volume ul | ~33 | ~85 |
| Bladder volume/system volume | +85% | ~30% |
| Total air volume in bladder as % of bladder potential | +85% | +50% |
| Bladder volume change caused by a 10 mmHg pressure change | 1.6% | 3.4% |
| Operating life | +20 hours | +12 hours |

[1]Net of stent within bladder
[2]The residual air is defined by the ICP level

Although both the flexible catheter design and the Spiegelberg design rely on an underfilled bladder to sense ICP, they are quite different in fundamental respects. The brain trauma of the flexible catheter is less in that the gas volume in the bladder of the present invention is about ⅕ that of prior art. Operating life is extended as the total air volume of the bladder is +50% of its potential volume vs. ~25% for Spiegelberg. The ability to more fully fill the bladder as a result of reducing dead space is an essential element in the ability of the bolt or flexible catheter system's ability to function with a manual pump. The system uses a tip-mounted butyl bladder to gain the benefits explained in the bolt version.

The flexible catheter has three defining aspects. Length is limited to ~45 cm, the total air volume in the bladder is about 25 ul, the starting bladder volume is +50% of its potential volume and the operating life exceeds 12 hours. The relevance of each defining aspect is as follows.

1. Catheter length is ~45 cm. This criterion requires that the transducer be located adjacent to the patient and confers the benefits of limited dead space to the system.
2. Starting bladder volume of 25 ul. The bladder displaces 25-ul of brain volume when the catheter is initially connected to the transducer, a volume significantly below the 100–125 ul of the prior art. The bladder volume restriction indirectly limits catheter length by the effect of dead space on bladder function. As catheter length increases, the bladder must be underfilled to a greater extent, the available air decreases, surface area increases and stoke increases. The unfavorable change in these three parameters reduces operating life. A catheter length much beyond 46 cm or 18 inches would decrease operating life or require a larger bladder.
3. The air volume of the bladder is 50% or more of its potential volume when the catheter is first connected to the transducer. The percent underfill required to limit wall motion is defined by dead space which in turn is defined by catheter length. This criterion thereby constrains catheter length in terms of available air and its affect on operating life.
4. The minimum operating life is eight hours. An operating life of less than eight hours is more burdensome to the nursing staff and would not be less well received.

A second purpose of the invention is to increase the operating life of the bladder so a manual pump can be used in lieu of an electromechanical pump. Four elements combine to extend operating life to over 12 hours. The first element is a five-fold reduction in bladder surface area. Surface area drops from 3.5 cm sq. in the case of the Spiegelberg bladder to 0.7 cm sq. in the bladder of the present invention. The reduction in surface area has a proportional effect on air loss and water ingress. The second element is the reduced stroke of the bladder caused by a reduction in dead space. The volume change, $(V_1-V_2)V_1$ required to express a waveform with a 10 mmHg pulse pressure is reduced from ~8% in the Spiegelberg design to 1.5% for the bolt and 3.4% of the catheter version of the present invention. The reduced stroke allows the bladder to work in a more nearly depleted condition and thereby extends operating life. The third element is the use of a tip-mounted bladder shown in FIG. 3 in lieu of the sleeve bladder now used. A tip-mounted bladder converts the air sequestered in a sleeve bladder into useable air and does not suffer a reduction in air volume due to the presence of a catheter body. The final element is the use of a butyl rubber bladder rather than a polyurethane bladder. Butyl reduces air loss by a factor of 5 and reduces water ingress by two orders of magnitude. The flaccid character of butyl as opposed to other rubber compounds makes butyl ideal in that it exhibits a very high frequency response and a low collapsing pressure. The low collapsing pressure allows the use of a thicker wall without introducing a pressure offset. The thicker wall in turn is critical in achieving one shift operation.

The introduction of a tip-mounted bladder in brain tissue presents a problem. The bladder cannot resist the force encountered during insertion into the brain and will fold back on itself. The matter of introducing a flaccid bladder into the brain is addressed by the use of a stent 21. The stent has enough column strength to resist axial forces encountered yet is small in diameter. Stent diameter is a critical parameter. The stent body displaces bladder air and reduces useable air as the bladder collapses incompletely around the stent. It has been found that a 0.5 mm diameter stent such as that shown FIG. 3c and FIG. 3e provides adequate column strength to withstand the forces encountered in passage through brain tissue and works well in a 1.8 mm diameter distal ICP catheter bladder. For ease of construction, the stent is created by extending the capillary tube 23 to the distal end of the bladder. Other stent constructions can also be used such as the two-legged U-shaped stent shown in FIG. 3d wherein each leg of the U is about 0.25 mm. In a U stent construction, the proximal end of the legs are imbedded in the plastic sleeve 22 to anchor the stent. This configuration is more flexible and particularly suited for use in the flexible catheter as it accommodates the flexure required to steer the catheter a plane parallel to the skull if desired.

Several options are available to insure that the stent will not pierce the bladder during insertion. In the case of a U stent, the contact area of the curved section of the U design provides adequate area to protect against wall damage. For reasons related to ease of manufacturing, the preferred embodiment in the bolt version of the present invention is as follows. A series of holes, 26, are drilled in that portion of the capillary tube that resides in the bladder to provide a plurality of air passages. A droplet of UV adhesive is applied to the distal end of the stent to form a rounded end. It has been found that a 0.045 diameter droplet provides a sufficient area to preclude penetration of the bladder by the stent.

The bladder stent described differs from a conventional catheter stylet in both geometry and function. A conventional catheter stylet is typically about the same diameter as the lumen in which it is placed. A bladder stent, in contrast, must be a fraction of the diameter of the bladder it supports to avoid displacing bladder air and affecting collapsing efficiency. Secondly, a catheter stylet performs a guiding function and deals with lateral loads. A bladder stent, in contrast, essentially bears an axial load. Lastly, a catheter stylet has a constant diameter whereas a bladder stent has an enlarged distal area to avoid penetrating the thin wall of the bladder.

Regarding construction of a rubber bladder, it has been found that a 1.25 cm long, 1.8 mm diameter butyl rubber bladder with a wall thickness of about 0.05 mm will provide good diastolic and systolic pressure response while presenting an adequate barrier to water vapor and air diffusion.

The table 3 shows the elements of the bolt catheter and flexible catheter that, in combination, achieve two principal objectives: reduce brain trauma and enable the use of a manual pump.

TABLE 3

| Construct | Effect | Attribute | Benefit |
|---|---|---|---|
| Transducer on minimum length catheter | Reduce dead space | 1. Smaller bladder<br>2. Reduce stroke<br>3. Greater fill % | 1. Reduce brain trauma<br>2. Extend operating life<br>3. Extend operating life |
| Transducer on bolt | Reduce dead space | 1. Smaller bladder<br>2. Reduce stroke<br>3. Greater fill % | 1. Reduce brain trauma<br>2. Extend operating life<br>3. Extend operating life |
| Butyl bladder | Reduce diffusion of air and water | 1. Reduced air required for one shift operating life = small bladder.<br>2. Eliminate water ingress as a problem | 1. Reduce brain trauma<br>2. No need to purge water vapor |
| Stent in bladder | Use tip mounted bladder | Increase in % of useable air volume | Extend operating life |

At pressures below 20 mmHg, the reluctance of brain tissue to separate squeezes the bladder and can cause the pressure reading to be higher than true ICP. To insure that the reading is accurate at pressures less than 20 mmHg, the brain tissue wherein the bladder will reside is dissected before ICP monitoring begins. The dissection is accomplished by either of two methods. The bladder may be overfilled to create a dissected pocket somewhat larger than the volume of the bladder in its normal operating state. Alternatively, a rod somewhat larger than the bladder diameter may be inserted into the brain to form a suitable pocket. The rod method can be used in the version where the pressure coupling assembly is placed in the bolt after it is screwed into the skull. Either method requires that the dissection event last for about a minute.

Dissection by overfilling the bladder can be accomplished on any of the versions by placing a closed end cylinder of appropriate volume onto the piston. In the case of the version where the bolt and catheter are separate assemblies as shown in FIG. 4, a combination holder injector is used as shown in FIGS. 4b–4d. The pressure coupling assembly is a small part relative to the size of the surgeon's fingers. Therefore, an improvement in the present invention is to provide a combined holder and pump tool which, with the holder end secured to the piston on the catheter, enables manipulation and insertion of the catheter into the bolt cavity 32 shown in FIG. 4a. Once the catheter is locked in the bolt, the procedure tool 50 is inverted and placed on the piston 12. The airtight receiving chamber 55 causes a bolus of air to be injected into the bladder that is approximately 1.5–2× the normal volume injected by the normal pumping event of placing the transducer probe on the piston.

In the two-part version shown in FIG. 4, a dissecting rod 39 can be inserted through the bolt cavity 32 and into the brain to dissect a pocket in the brain. The pressure coupling assembly can then be inserted into the bolt and locked in place.

Another objective of the present invention is to allow the doctor to measure ICP with a minimally invasive catheter and later introduce a drainage catheter should drainage be required. Head trauma and certain operations result in swelling of brain tissue that can result in elevated intracranial pressure. If ICP rises above 20 mmHg for an extended period, the patient's well being is at risk. One of the more important therapies used to manage intracranial pressure is that of inserting a catheter into a ventricle and draining cerebral spinal fluid (CSF). The sole criterion for commencing drainage of CSF is that of an elevated ICP. Presently available means that measure pressure and drain CSF present a dilemma. The doctor must speculate at the beginning of the procedure as to whether or not drainage will be required and then chose one of two options based on that speculation. The first option is to insert a small 3 to 5 Fr pressure sensor 1 cm into the brain to monitor pressure. If the ICP data obtained suggests that drainage is required, a second hole must be drilled in the patient's skull to allow placement of a drainage catheter. The second option involves the insertion of a 9 Fr. drainage catheter into a ventricle located about 6 cm beneath the skull. The catheter is attached to a standard pressure line that extends to an external pressure transducer. The doctor can therefore measure pressure and, if need be, drain fluid. If ICP is not elevated enough to justify drainage, the patient has been subjected to a more invasive procedure than option one and obtained no benefit. The two options present a dilemma in that either procedure can be a good choice or a poor choice depending on the ICP encountered. The present invention solves the dilemma by use of a bolt that allows assessment of ICP by means of a small pressure-sensing catheter as a first step. If CSF drainage is called for, the bolt then allows placement of a drainage catheter as a second step. The invasiveness of the procedure is thereby tailored to the patient's need.

The invention utilizes a ventricular bolt assembly 8 as shown in FIG. 5. The assembly incorporates a pressure-coupling catheter identical to that described earlier except that it resides a side arm 61. The side arm construction moves the pressure sensing function to the side and keeps the center of the bolt available for insertion of a drainage catheter. The distal end of the coupling catheter resides in the periphery of the inner bore 64 of the bolt, as seen in FIG. 5b. Peripheral placement of the catheter preserves the center section of the inner bore for use by a drainage catheter.

The passageway formed by the anchor well 62 in combination with the inner bore 64 shown in FIG. 6 is large enough to allow a drainage catheter to be introduced into the brain at an angle to the axis of the inner bore. The angle at which a catheter can be introduced into the bolt is defined by the length and diameter of the inner bore and anchor well. The following dimensions allow a 2.2-mm drainage catheter to enter the brain at an angle of 15 degrees. The outer diameter of the bolt portion inserted into the skull is 6.5 mm, the inner bore diameter is 4.4 mm and the height and diameter of the anchor well are 1.5 cm and 1 cm respectively. It will be appreciated that the dimensions of the elements that control the angulation of the catheter can be changed from those cited to vary the maximum angle of entry.

The coupling catheter is positioned into or against the wall of the inner bore to preserve space for maneuvering the drainage catheter. Off-center placement of the coupling catheter influences the manner in which the bolt is fixed in the skull. Previously used bolts have been fixed in the skull by a threaded section such as the bolt thread 16 of FIG. 4. A threaded engagement cannot be used in the present invention in that the eccentric catheter will orbit within brain tissue as the bolt is screwed in place. Although a transition device could be screwed into the skull and the bolt attached to the device, the preferred embodiment is to use a rib set 17 made of deformable material such as polycarbonate and tap the bolt directly in the skull with a mallet. In addition to allowing linear insertion of the bolt into the skull to avoid brain trauma, the rib set also provides a more effective bacteria barrier than a threaded element. The ribs provide a series of radial barriers to the passage of microbes whereas a threaded element presents a spiral pathway between the root of the thread and the skull. The ribs in this design extend beyond the body of the bolt approximately 0.25 mm and provide interference pressure against the skull sufficient to secure the bolt in place.

It is not uncommon for a drainage catheter to become clogged by brain tissue or blood clots. The accepted procedure for clearing an obstruction is to inject 1 cc of saline through the catheter. The injected volume is quite small as a larger volume could significantly increase ICP if the injectate flows into the brain but is blocked from draining back out. If the attempt to clear the catheter fails, the doctor must either insert a new catheter through a new craniotomy or relinquish the possibility of draining. The risk of infection is such that hospital protocol discourages inserting a second catheter in an existing drill hole.

The present invention combines several design elements shown in FIGS. 5–7 to provide a system wherein a clogged catheter can be replaced without undue risk of infection. The first element is a catheter anchor sleeve 71 approximately 1 cm long with a sleeve flange 72 and a compression cap 70. The second element is an anchor well 62 with a well face 63 that is flat and approximately 1 mm wide. The anchor sleeve keeps the well face sterile until a decision is made to insert a drainage catheter. The anchor sleeve and cap are placed on the proximal end of the catheter in the manufacturing process. Once the catheter is placed in the ventricle, the anchor sleeve is moved into the well and the compression cap screwed down. The compression force produced by the sleeve secures the catheter in place and effects a barrier to the movement of bacteria down the wall of the well and across the face of the top surface of the well. As a further barrier to bacteria entry, a flange 72 is filled or coated with an antimicrobial agent such as Betadine ointment. When the catheter is removed, friction between the anchor and the catheter cause the anchor to be withdrawn with the catheter. The top surface and the sidewall of the well are sterile at this time. The sterile surface precludes the possibility of contaminating the catheter during the introduction of a replacement catheter.

Infections related to ICP monitoring present a grave risk to the patient since the blood brain barrier makes the usual systemic administration of antibiotics ineffective. The concern level is high enough among doctors that some choose to avoid ICP monitoring altogether on the basis that the risk and consequence of infection exceeds the benefit of monitoring. In order to minimize the risk of infection, most currently used ventricular catheters are tunneled beneath the scalp for 3–4 cms. The scalp serves as a barrier to the ingress of bacteria. The infection rate of a tunneled catheter is about 1%. The infection rate of a bolt-based system, in contrast, is about 4%. In spite of the fact that bolt based systems have four times the rate of infection as tunneled catheters, currently available bolt systems do not incorporate any specific antimicrobial features.

The present invention incorporates a number of provisions that explicitly address the risk of infection. Current bolt systems screw into to the skull. The root of the thread has a smaller diameter than he drill hole so the thread can move forward without jamming. The clearance presents a spiral access route for bacteria that extends from the scalp to the brain. The present invention substitutes a set of ribs for a threaded section. The radial ribs are slightly larger than the drilled hole. When inserted into the skull, the compressive force between the ribs and the hole serves to fix the bolt in the skull. The compressive force also acts as a physical barrier to the movement of bacteria down the drill hole.

The ribs also serve as an applicator to apply an antimicrobial agent to the surfaces of the drilled hole in that the agent is trapped between ribs and delivered deeply into the drill hole. Agent trapped in the space between the ribs elutes out over time and provides long term protection. The threads of a screw can also serve as an applicator and reservoir for agent. The spiral wiping motion of a thread entering the drill hole, however, causes most of the antimicrobial agent to remain near the top of the drill hole. Alternatively, a silver ion emitting coating may be applied to the outer surface of either the rib or screw version and provide the same effect. None of the prior art bolts apply an antimicrobial agent to the surface of the drill hole.

The third and fourth antimicrobial provisions are directed toward the drainage catheter. The catheter anchor sleeve 71 has a flange 72 that covers the face of the anchor well. The flange has a groove 73 in the surface that contacts the anchor well face 63. The groove is filled with an antimicrobial agent such as Betadine ointment to add a chemical barrier to the physical barrier presented by a compressed elastomeric surface against the well face. The flange preserves the sterility of the face of the well and reduces the likelihood that a replacement catheter will become contaminated during insertion into the bolt.

Although the invention description has focused on the measurement of ICP, it will be appreciated that the concepts described can be used in many other pressure measurement applications such as measuring compartment pressure in a muscle bed. In the case of measuring compartment pressure in muscle beds, an adapter with the proximal characteristics of the IP bolt described would be anchored to the skin by an adhesive patch. The stent of the catheter would extend through the bladder as in a construction similar to that in FIG. 3e. The stent would extend beyond the bladder and terminate in a sharp pointed end to make possible the introduction of the bladder into a muscle bed. The reduction in the connecting lumen air volume achieved by integrating the bolt, transducer and catheter would make it possible to use a small bladder to measure compartment pressure.

Although the invention describes the use of an inner bore as a passageway to introduce a drainage catheter into the brain, it will be appreciated that the passageway could be used to introduce other catheters. For example, catheters could be introduced to that measure other parameters such as $pO^2$ or to sample tissue. The inner bore is large enough that the alternative probe can be introduces alone or in combination with a drainage catheter. The design also allows a first catheter with a first function be replaced by a second catheter with a second function in a manner that minimizes risk of infection.

It is understood that the preceding description is given merely by way of illustration and not in limitation of the invention and that various modifications may be made thereto without departing from the spirit of the invention as claimed.

What is claimed is:

1. A system for monitoring pressure within a mammalian body, the system comprising:
    a catheter having a proximal end, a distal end, and an outer surface configured for insertion into the mammalian body with the distal end of the catheter positioned within the mammalian body;
    a first lumen, filled with a gas, extending longitudinally through the length of the catheter, the lumen providing gaseous communication between the distal end and the proximal end 23 of the catheter;
    a flaccid bladder, containing a gas, positioned at the distal end of the catheter, the bladder being in gaseous communication with the first lumen and being of a size configured for collapsing and expanding in response to changing pressure in the body so that a pressure change in the gas within the bladder reflects the pressure change within a body space in which the bladder is placed, the first lumen being thereby operable to transmit, in the gas from the distal end to the proximal end of the catheter, changes in pressure exerted against the bladder;
    a pressure transducer mounted on the proximal end of the catheter, the pressure transducer being in gaseous communication with the first lumen; and
    a second lumen, filled with the gas, positioned between the proximal end of the catheter and the pressure transducer and in gaseous communication there between;
    wherein the total gas volume of the bladder represents no less than approximately 50% of the gas volume contained in the total system.

2. The system of claim 1 wherein the gas volume in the bladder represents approximately 75% of the gas volume contained in the total system so as to extend the operating life of the bladder.

3. The system of claim 1 further comprising an adapter capable of being affixed to the body, wherein the catheter and the pressure transducer are integrated with the adapter so as to minimize the gas volume in the second lumen connecting the catheter and pressure transducer.

4. The system of claim 3 wherein the adapter is a bolt capable of being affixed to the skull.

5. The system of claim 4 wherein the outer surface of the adapter comprises a set of at least two ribs each having a diameter slightly larger than the hole in the skull such that inserting the adapter in the hole will establish a compressive force sufficient to hold the adapter securely to the skull.

6. The system of claim 4 further comprising a piston lumen fixed in the bolt, tie piston lumen being in gaseous communication with the catheter, and a transducer housing configured for housing the pressure transducer, the housing provided with a hollow cylindrical segment that constitutes a female portion of an air pump, the cylindrical segment configured to be inserted in the bolt, the cylindrical segment being configured to receive a piston formed by the proximal end of the catheter or any adapting extension thereof and a sealing means between the piston and cylinder so that when the transducer housing engages the piston, the piston automatically pumps a desired amount of air into the bladder.

7. The system of claim 1, wherein the bladder is formed of material selected from the group of materials consisting of:

a) buna N
b) Nitrile
c) Neoprene
d) Butyl rubber.

8. A system for monitoring pressure within a mammalian body, the system comprising:
   a catheter having a proximal end, a distal end, and an outer surface configured for insertion into the mammalian body with the distal end of the catheter positioned within the mammalian body;
   a lumen, filled with a gas, extending longitudinally through the length of the catheter, the lumen providing gaseous communication between the distal end and the proximal end of the catheter;
   a flaccid bladder, having an elongate shape and filled with a gas, positioned on the distal end of the catheter, the bladder being in gaseous communication with the lumen and being of a size configured for expanding in response to changing pressure in the body so that a pressure change in the gas within the bladder reflects the pressure change within a body space in which the bladder is placed, the lumen being thereby operable to transmit, in the gas from the distal end to the proximal end of the catheter, changes in pressure exerted against the bladder;
   a stent anchored in the distal end of the catheter and positioned within the bladder so that the stent extends most of the length of the bladder so that the stent is configured for maintaining the elongate shape of the bladder as the bladder encounters resistive tissue; and
   a device configured to limit the penetrating force between the stent and the distal end of the bladder such that the force generated by the stent on the bladder during the act of introducing the bladder into a brain does not exceed the ability of the bladder to resist being pierced.

9. The system of claim 8 wherein gas volume occupied by the stent is approximately 30% or less of the volume of the bladder.

10. The system of claim 8 wherein the stent comprises a single support member that is approximately 0.5 mm in diameter and having a tip of the stent enlarged to avoid penetration of the bladder.

11. The system of claim 8 wherein the stent comprises a U-shaped member having two legs and each of the two legs is approximately 0.25 mm in diameter.

12. A system for monitoring intracranial pressure in a brain inside a skull of a mammalian body, the system comprising:
   a bolt having a device for affixing the bolt to the skull, an inner bore resident within the bolt configured for receiving a drainage catheter therein, the bore being of sufficient diameter to allow the drainage catheter to enter the brain at an appreciable angle to a centerline of the inner bore, and an outer bore within the bolt offset from the inner bore, the outer bore configured for receiving a sensing catheter therein;
   a sensing catheter positioned within the outer bore such that the sensing catheter extends from the bolt into the brain for the purpose of sensing and responding to pressure within the brain;
   a pressure transducer adapted to attach to the sensing catheter, the pressure transducer positioned adjacent to said bolt;
   a drainage catheter positioned within the inner bore so that the sensing catheter and the drainage catheter are capable of operating within the bolt simultaneously; and
   a device for engaging the drainage catheter in the inner bore to anchor the drainage catheter to the bolt and to provide a fluid seal there between.

13. The system of claim 12 wherein the angle is in the maximum range of about 15 degrees.

14. The system of claim 12 wherein the bolt is provided with a well through which the drainage catheter passes, the well having an external threaded portion and a top well face, and further comprising:
   a compression cap configured to engage the external threaded portion to secure the drainage catheter to the bolt;
   an anchor sleeve positionable within the well; and
   wherein insertion of the anchor sleeve into the well and tightening of the compression cap secures the drainage catheter to the bolt and restricts the ability of bacteria to reach the well surfaces contacted by the anchor sleeve.

15. The system of claim 14 wherein a flange formed on the anchor sleeve is at the proximal end of the anchor sleeve so that the insertion of the anchor sleeve into the well and the tightening of the compression cap compresses the flange against the well face to prevent ingress of bacteria.

16. The system of claim 15 wherein the flange further comprises an element adapted to carry an antimicrobial agent configured to be secured between the flange surface and the well in a manner that insures that the antimicrobial agent is in contact with the well.

17. The system of claim 14 wherein the anchor sleeve is engaged with either the drainage catheter or the compression cap in a manner that insures that the anchor sleeve will be withdrawn from the well as the catheter is withdrawn from the brain.

18. An applicator for applying an antimicrobial agent to a cut surface of a drill hole, the applicator comprising:
   an element for fixing a bolt to the skull, the element configured to fit within the drill hole in a manner that at least a portion of the element engages the cut surface of the drill hole, the element having an outer surface having at least one irregularity of the surface; and
   a coating of an antimicrobial agent placed within the at least one irregularity of the surface of the element such that the introduction of the element into the drill hole and its continuing residence in the hole will result in the transferring of a portion of the agent to the cut surface of the drill hole.

19. The applicator of claim 18 wherein the outer surface of the element consists of a series of circular ribs encircling the element; and
   wherein the irregularity of the surface comprises each of the ribs being separated from an adjacent rib by a space between the ribs.

20. The applicator of claim 18 wherein the outer surface of the element consists of a helical thread encircling the element.

21. An applicator for applying an antimicrobial agent to a surface of a skull between the skull and a skull bolt inserted in the skull, the applicator comprising an element containing an antimicrobial agent, the element configured to be secured between the skull bolt and the skull in a manner that insures that the antimicrobial agent is in contact with the skull.

22. The applicator of claim 21 wherein the element is a gasket formed of a porous material impregnated with an antimicrobial agent.

23. A method for measuring intracranial pressure in a mammalian body comprising:

providing an air column catheter including a flaccid bladder externally secured to a distal end of air column catheter;

coupling the air column catheter with a pressure transducer into an adapter configured to be affixed to the mammalian body;

affixing the adapter to the mammalian body, with the catheter inserted within the skull of the mammalian body; and sensing the intracranial pressure in the mammalian body utilizing the catheter and the pressure transducer.

24. The method of claim 23 further comprising inserting a drainage catheter into the mammalian body; and draining a portion of the mammalian body with the drainage catheter.

25. A system for monitoring pressure within a mammalian body, the system comprising:

a pressure sensing arrangement designed to be inserted into the mammalian skull for sensing pressure therein including a flaccid bladder externally secured to a distal end of the arrangement;

a mounting assembly designed to be mounted directly to the mammalian body in close proximity to the insertion point of the pressure sensing arrangement; and a pressure transducer configured for translating a pressure signal received from the pressure sensing arrangement into an electrical signal, said pressure transducer mounted on the mounting assembly and operatively connected with the pressure sensing arrangement.

26. A method of monitoring pressure within a mammalian body, comprising the steps of:

inserting a pressure sensing arrangement into the mammalian skull for sensing pressure therein including a flaccid bladder externally secured to a distal end of the arrangement;

connecting a mounting assembly directly to the mammalian body in close proximity to the insertion site of the pressure sensing arrangement;

mounting a pressure transducer in close proximity to the mounting assembly and operatively connecting the transducer with the pressure sensing arrangement;

translating a pressure signal received from the pressure sensing arrangement into an electrical signal; and monitoring pressure within the mammalian body utilizing the pressure sensing arrangement and the pressure transducer.

27. The method according to claim 26 wherein the flaccid bladder is air-filled.

28. The method according to claim 26 wherein the transducer is operatively connected to the pressure sensing assembly through a single passageway within the mammalian body between the transducer and the pressure sensing assembly and further comprising the step of inserting a drainage tube at least in part through the single passageway and draining liquid from the mammalian body using the drainage tube.

29. The method according to claim 26 wherein the transducer is operatively connected to the pressure sensing assembly through a single passageway within the mammalian body between the transducer and pressure sensing assembly, wherein the mounting assembly includes an elongated, tubular fastening member having longitudinally spaced annular ribs extending around the outer surface of the member, and further comprising the step of inserting the fastening member into the passageway in a friction fitting manner.

30. A method of monitoring pressure within a mammalian body, comprising the steps of:

inserting a pressure sensing arrangement into the mammalian body for sensing pressure therein;

connecting a mounting assembly directly to the mammalian body in close proximity to the insertion site of the pressure sensing arrangement;

operatively connecting a transducer with the pressure sensing assembly through a single passageway within the mammalian body between the transducer and pressure sensing assembly;

introducing an antimicrobial agent into the passageway;

translating a pressure signal received from the pressure sensing arrangement into an electrical signal; and monitoring pressure within the mammalian body utilizing the pressure sensing arrangement and the transducer.

31. A fixture enabling access of at least two medical instruments to an intercranial target site comprising:

at least one lumen sized to receive a pressure monitoring device;

at least one lumen sized to receive a drainage catheter;

a shank section through which said lumens extend; and a bacteria barrier disposed on said shank, said barrier configured to be coupled to a pressure sensing transducer and configured to contact skull tissue in a region near said intercranial target site.

32. A method of monitoring intercranial pressure, comprising:

creating an access opening in the skull of a subject;

providing a mounting assembly having an anchor sleeve with an inner lumen disposed within an inner bore of the mounting assembly;

attaching the mounting assembly to the skull of the subject proximal to the access opening;

identifying a conduit having a bladder secured to a distal end of said conduit;

placing said conduit through the inner lumen of the anchor sleeve such that said distal end of said conduit is located at a target intercranial site;

positioning a terminal end of said conduit at a location near said access opening;

attaching said terminal end of said conduit to a pressure transducer such that said pressure transducer is in fluid communication with said bladder; and determining the pressure at said target intercranial site by monitoring the pressure in said bladder.

33. An assembly for monitoring intercranial pressure of a mammal comprising:

a mounting fixture sized for fixation on a subject mammal;

a hollow conduit extending from said mounting fixture a sufficient distance to place said hollow conduit at a desired pressure monitoring site and having a length less than or equal to about 45 cm;

a pressure transducer placed in fluid communication with said hollow conduit, said pressure transducer located in close proximity to said mounting fixture; and a thin-walled, substantially non air-permeable bladder externally secured to a distal end of said hollow conduit, said bladder being in fluid communication through said hollow conduit with said pressure transducer.

34. A system for monitoring intercranial pressure of a mammal comprising:

a mounting fixture sized for placement on a subject, said mounting fixture having a passageway extending substantially along the length of said mounting fixture;

a conduit sized for communication with said passageway of said mounting fixture and having a distal end, a proximal end and a length less than or equal to about 45 cm;

an inflatable bladder mounted toward said distal end of said conduit;

said conduit sized such that said distal end extends to a target pressure monitoring site and said proximal end terminates at a location near said mounting fixture; and a pressure transducer sized for fluid connection to said conduit, said pressure transducer positioned adjacent to said mounting fixture and in communication with said conduit.

35. A system for monitoring pressure within a mammalian body, comprising:

a catheter having a proximal end, a distal end, a length less than or equal to about 45 cm and an outer surface configured for insertion into the mammalian body with the distal end of the catheter positioned within the mammalian body;

a lumen, filled with a gas, extending longitudinally through the length of the catheter, the lumen providing gaseous communication between the distal end and the proximal end of the catheter;

a flaccid bladder, containing a gas, positioned at the distal end of the catheter, the bladder being in gaseous communication with the lumen and being of a size configured for collapsing and expanding in response to changing pressure in the body so that a pressure change in the gas within the bladder reflects the pressure change within a body space in which the bladder is placed, the lumen being thereby operable to transmit, in the gas from the distal end to the proximal end of the catheter, changes in pressure exerted against the bladder; and a pressure transducer mounted adjacent to the proximal end of the catheter, the pressure transducer being in gaseous communication with the lumen.

36. The system of claim 35 wherein the gas volume in the bladder represents approximately 75% of the gas volume in the system.

37. The system of claim 35 further comprising an adapter capable of being affixed to the body, wherein the catheter and the pressure transducer are integrated with the adapter so as to minimize the gas volume in the lumen connecting the catheter and pressure transducer.

38. The system of claim 37 wherein the adapter is a bolt capable of being affixed to a skull of the mammalian body.

39. The system of claim 38 wherein the adapter comprises an elongated, tubular fastening element with an outer surface wherein the outer surface consists of a set of ribs consisting of at least two ribs each having a diameter slightly larger than a hole in the skull such that inserting the bolt in the hole will establish a compressive force sufficient to hold the bolt securely to the skull.

40. The system of claim 38 further comprising a piston lumen fixed in the bolt the piston lumen being in gaseous communication with the catheter, and a transducer housing configured for housing the pressure transducer, the housing provided with a hollow cylindrical segment that constitutes a female portion of an air pump, the cylindrical segment having a distal end adapted to be inserted in the bolt and a proximal end adjacent to the pressure transducer, the cylindrical segment being configured to receive a piston formed by the proximal end of the catheter or any adapting extension thereof and a sealing means between the piston and cylinder so that when the transducer housing engages the piston, the piston automatically pumps a desired amount of air into the bladder.

41. The system of claim 35, wherein the bladder is formed of material selected from the group of materials consisting of:

a) buna N
b) Nitrile
c) Neoprene
d) Butyl rubber.

42. The system of claim 35 wherein said pressure transducer is configured to be attached to the body of a patient proximate to said proximal end of said catheter.

43. An applicator for applying an antimicrobial agent to a surface of a skull between the skull and a skull bolt inserted in the skull, the applicator comprising a gasket formed of a porous material impregnated with an antimicrobial agent, the gasket configured to be secured between the skull bolt and the skull in a manner that insures that the antimicrobial agent is in contact with the skull.

44. A method of monitoring pressure within a mammalian body, comprising:

inserting a pressure sensing arrangement into the mammalian body for sensing pressure therein;

connecting a mounting assembly directly to the mammalian body in close proximity to the insertion site of the pressure sensing arrangement;

mounting a pressure transducer in close proximity to the mounting assembly and operatively connecting the transducer with the pressure sensing arrangement through a single passageway within the mammalian body between the transducer and the pressure sensing arrangement;

inserting a drainage tube at least in part through the single passageway and draining liquid from the mammalian body using the drainage tube;

translating a pressure signal received from the pressure sensing arrangement into an electrical signal; and monitoring pressure within the mammalian body utilizing the pressure sensing arrangement and the pressure transducer.

45. A method of monitoring pressure within a mammalian body, comprising:

inserting a pressure sensing arrangement into the mammalian body for sensing pressure therein;

connecting a mounting assembly including an elongated tubular fastening member having longitudinally spaced annular ribs extending around the outer surface of the member directly to the mammalian body in close proximity to the insertion site of the pressure sensing arrangement;

mounting a pressure transducer in close proximity to the mounting assembly and operatively connecting the transducer with the pressure sensing arrangement through a single passageway within the mammalian body between the transducer and the pressure sensing arrangement;

inserting the fastening member into the single passageway in a friction fitting manner;

translating a pressure signal received from the pressure sensing arrangement into an electrical signal; and monitoring pressure within the mammalian body utilizing the pressure sensing arrangement and the pressure transducer.

46. A system for monitoring pressure within a mammalian body, comprising:
- a catheter having a proximal end, a distal end, and an outer surface configured for insertion into the mammalian body with the distal end of the catheter positioned within the mammalian body;
- a lumen, filled with a gas, extending longitudinally through the length of the catheter, the lumen providing gaseous communication between the distal end and the proximal end of the catheter;
- a flaccid bladder, containing a gas, positioned at the distal end of the catheter, the bladder being in gaseous communication with the lumen and being of a size configured for collapsing and expanding in response to changing pressure in the body so that a pressure change in the gas within the bladder reflects the pressure change within a body space in which the bladder is placed, the lumen being thereby operable to transmit, in the gas from the distal end to the proximal end of the catheter, changes in pressure exerted against the bladder and the bladder having approximately 75% of the gas volume of the system; and
- a pressure transducer mounted adjacent to the proximal end of the catheter, the pressure transducer being in gaseous communication with the lumen.

* * * * *